(12) United States Patent
Takizawa et al.

(10) Patent No.: US 8,306,592 B2
(45) Date of Patent: Nov. 6, 2012

(54) CAPSULE MEDICAL DEVICE

(75) Inventors: Hironobu Takizawa, Hachioji (JP); Hironao Kawano, Hachioji (JP); Akio Uchiyama, Yokohama (JP); Hidetake Segawa, Hachioji (JP); Masatoshi Homan, Hino (JP)

(73) Assignee: Olympus Corporation, Tokyo (JP)

( * ) Notice: Subject to any disclaimer, the term of this patent is extended or adjusted under 35 U.S.C. 154(b) by 2078 days.

(21) Appl. No.: 11/013,178

(22) Filed: Dec. 15, 2004

(65) Prior Publication Data

US 2005/0177069 A1 Aug. 11, 2005

(30) Foreign Application Priority Data

Dec. 19, 2003 (JP) .................................. 2003-423524
Jan. 8, 2004 (JP) .................................. 2004-003503

(51) Int. Cl.
*A61B 5/1455* (2006.01)
(52) U.S. Cl. ........................ 600/310; 600/322
(58) Field of Classification Search .......... 600/309–344, 600/345, 347, 361; 422/44, 82.02, 125; 436/150, 436/171
See application file for complete search history.

(56) References Cited

U.S. PATENT DOCUMENTS 4,011,538 A * 3/1977 Froemel .......................... 338/35
7,289,836 B2 * 10/2007 Colvin, Jr. ..................... 600/316
2002/0072784 A1 6/2002 Sheppard, Jr. et al.
2002/0111544 A1 8/2002 Iddan
2002/0132226 A1 9/2002 Nair et al.
2002/0146368 A1 10/2002 Meron et al.
2002/0165444 A1 11/2002 Whitman
2002/0198470 A1 12/2002 Imran et al.

FOREIGN PATENT DOCUMENTS

| | | |
|---|---|---|
| CN | 1328638 | 12/2001 |
| DE | 198 58 426 A1 | 9/1999 |
| EP | 0 554 955 A1 | 8/1993 |
| GB | 2 373 330 A | 9/2002 |
| JP | 5-200015 | 8/1993 |
| JP | 2005-192879 | 7/2005 |
| JP | 2006-509574 | 3/2006 |
| WO | WO 97/33513 | 9/1997 |
| WO | WO 99/48419 | 9/1999 |
| WO | WO 01/69212 A1 | 9/2001 |
| WO | WO 02/07598 A1 | 1/2002 |
| WO | WO 02/49507 A1 | 6/2002 |
| WO | WO 2004/014227 A1 | 2/2004 |
| WO | WO 2004/054430 A2 | 7/2004 |

OTHER PUBLICATIONS

Supplementary European Search Report dated Jun. 7, 2010.
Chinese Office Action dated Nov. 6, 2009.

* cited by examiner

*Primary Examiner* — Eric Winakur
*Assistant Examiner* — Marjan Fardanesh
(74) *Attorney, Agent, or Firm* — Scully, Scott, Murphy & Presser, P.C.

(57) ABSTRACT

A capsule casing of a capsule medical device has a chemical sensor inside, used for sensing operation. The chemical sensor has a recovery device which resets the chemical sensor to an initial state thereof so as to use the chemical sensor for the sensing operation a plurality of times or continuously.

8 Claims, 18 Drawing Sheets

FIG. 13A
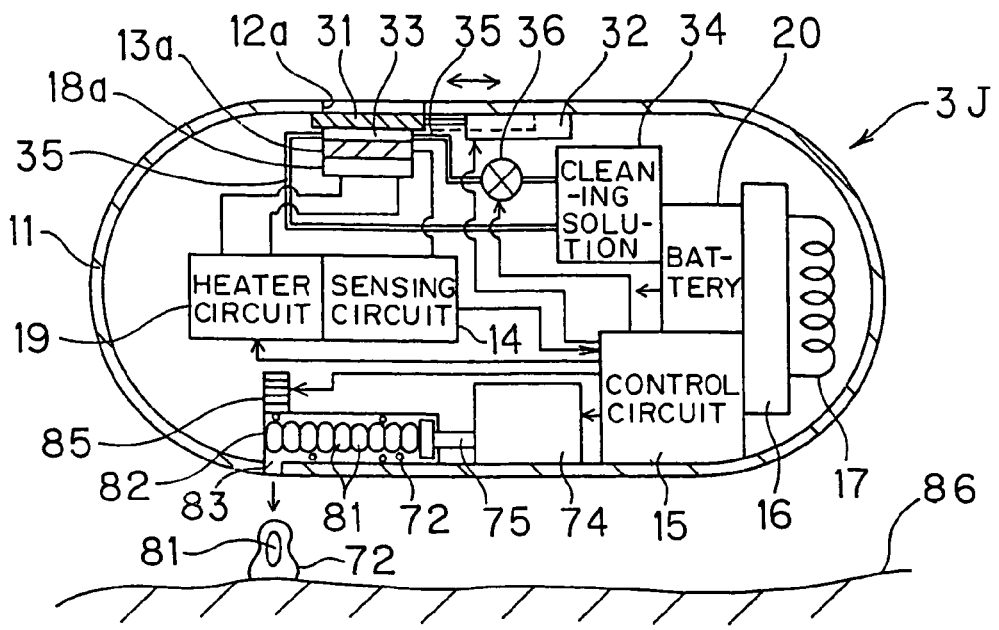
FIG. 13B
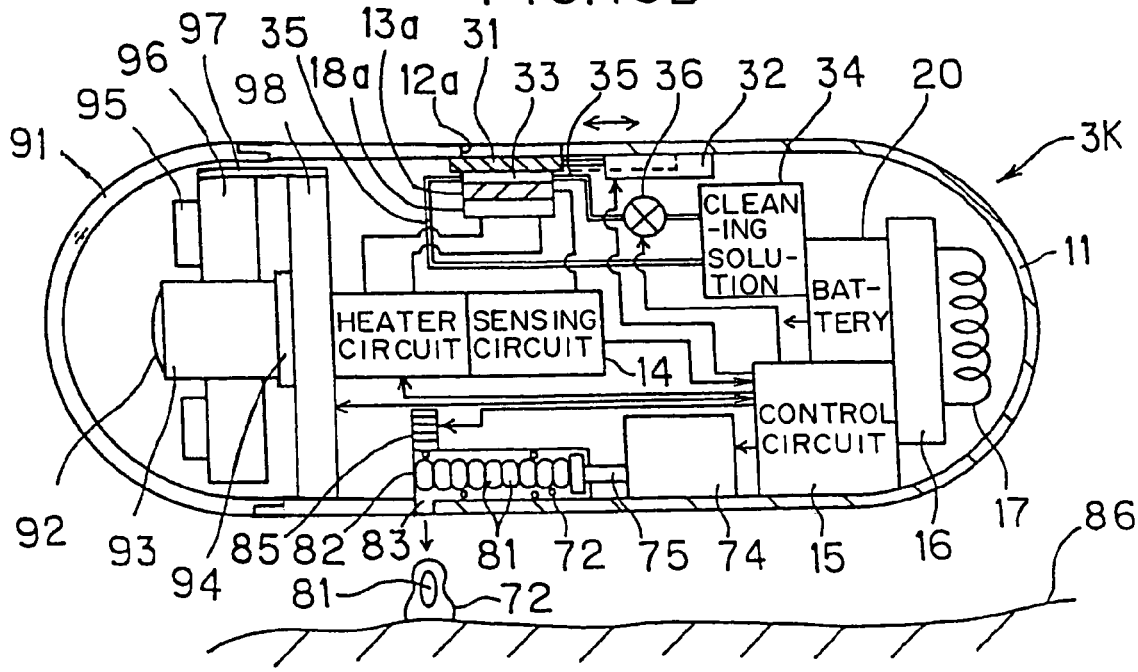
FIG. 13C
| SENDING DATA | IMAGE DATA Dg | SENSING DATA Dc |

CAPSULE MEDICAL DEVICE

This application claims benefit of Japanese Application Nos. 2003-423524 filed on Dec. 19, 2003, and 2004-003503 Jan. 8, 2004, the contents of which are incorporated by this reference.

BACKGROUND OF THE INVENTION

Field of the Invention

The present invention relates to a capsule medical device including a chemical sensor for examining the body fluid in the body.

Recently, various capsule medical devices which are orally inserted in the body and examine the body are proposed.

Japanese Unexamined Patent Application Publication No. 5-200015 discloses a capsule device which sucks the body fluid in the body cavity and examines the sucked body fluid. According to the conventional art, the capsule device comprises a blood sensor which senses the blood.

SUMMARY OF THE INVENTION

A capsule medical device having a chemical sensor used for sensing operation, comprises:
 a capsule casing;
 a chemical sensor arranged in the capsule casing; and
 a recovery device which recovers the chemical sensor to an initial state thereof so as to use the chemical sensor for sensing operation a plurality of times or continuously.

BRIEF DESCRIPTION OF THE DRAWINGS

FIG. 13A is a diagram schematically showing the internal structure of a capsule medical device according to a second modification;

FIG. 13B is a diagram schematically showing the internal structure of a capsule medical device according to a third modification;

FIG. 13C is a diagram showing the data format sent from the capsule medical device according to the third modification;

DETAILED DESCRIPTION OF THE PREFERRED EMBODIMENTS

Hereinbelow, a description is given of embodiments of the present invention with reference to the drawings.

First Embodiment

A first embodiment of the present invention will be described with reference to FIGS. 1 to 7.

Figure 2A:
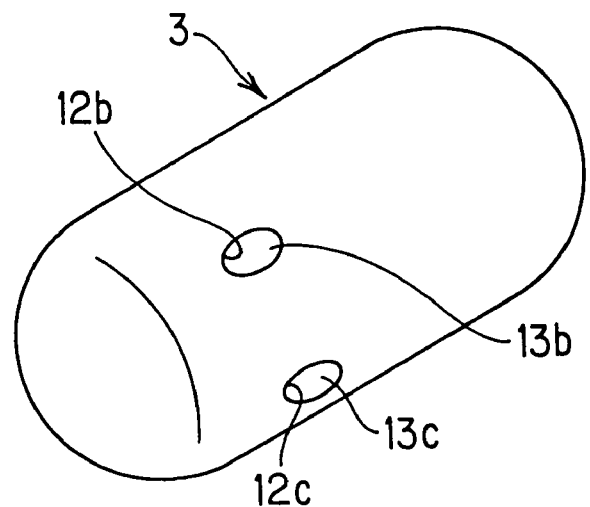
FIG. 2A is a perspective view showing the structure of a capsule medical device.
Figure 2B:
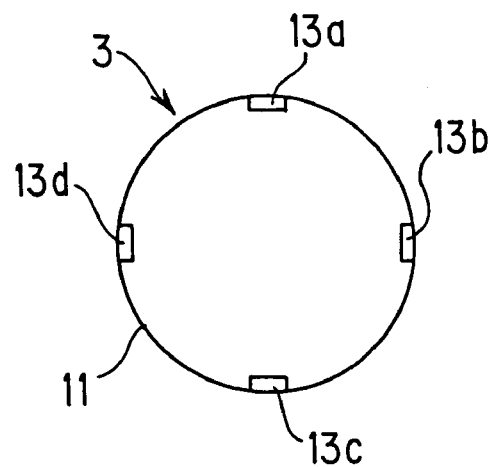
FIG. 2B is a diagram showing the arranging positions of chemical sensors in the capsule medical device.
Figure 2C:
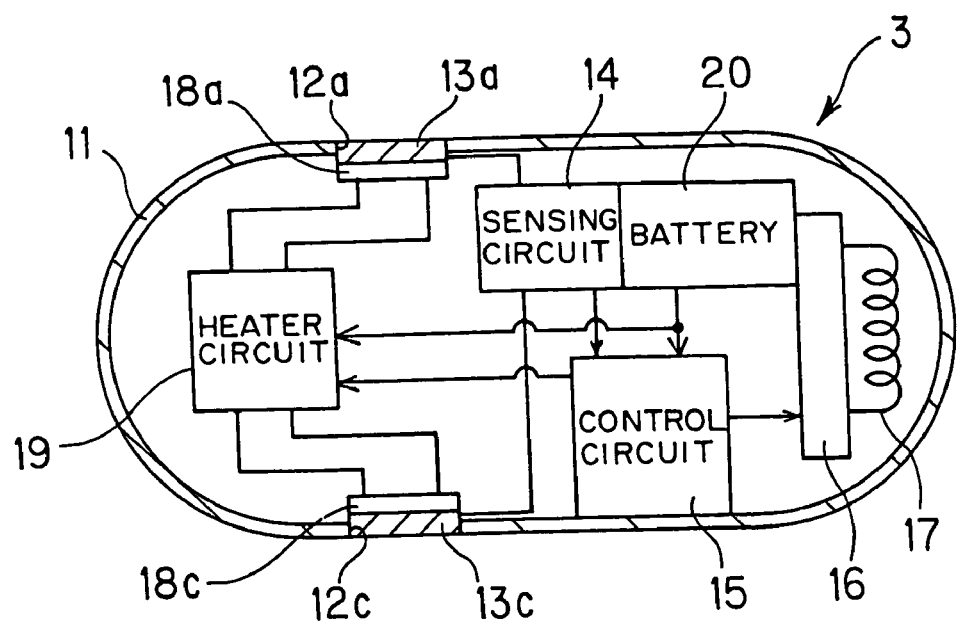
FIG. 2C is a longitudinal cross-sectional view showing the internal structure of the capsule medical device.

FIG. 2A is a diagram showing the appearance of a capsule medical device. FIG. 2B is a diagram schematically showing chemical sensors which are arranged at four positions on the outer circumferential surface of the capsule medical device. FIG. 2C is a cross-sectional view showing the internal structure of the capsule medical device.

Figure 1:
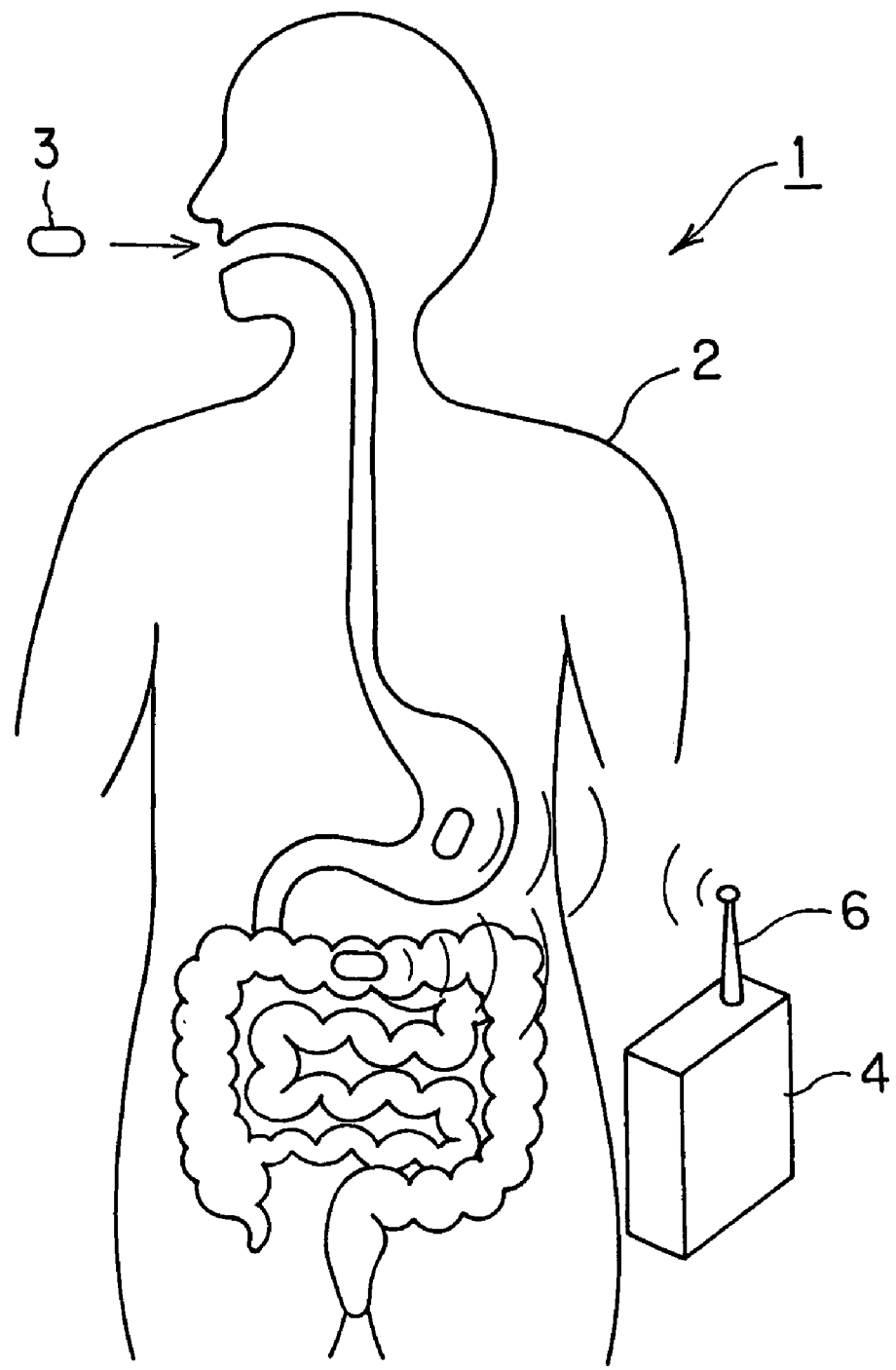
FIG. 1 is a diagram showing the structure of a capsule medical system as a using example according to a first embodiment of the present invention.

Referring to FIG. 1, a capsule medical system 1 comprises: a capsule medical device 3 which is swallowed by a patient 2 and comprises chemical sensors for examining whether or not the tumor or bleeding exists in the body; and an extracorporeal device 4 which receives, via an antenna 6, information sent by radio waves from the capsule medical device 3 and stores the information.

Referring to FIG. 2, the capsule medical device 3 comprises openings $12a$ to $12d$ at a plurality of positions of a capsule exterior case (or casing) 11, and each opening $12i$ ($i$=a to d) comprises a chemical sensor $13i$.

According to the first embodiment, chemical sensors $13a$ to $13d$ are arranged at, e.g., four positions on a cylindrical outer circumferential surface of the exterior case. The chemical sensor $13i$ has a sensor surface serving as the surface (top surface) thereof that is exposed at the opening $12i$ and the exposed sensor surface senses an examination target such as the blood, tumor, tumor marker, protein, carbohydrate, lipid, enzyme, drug, gene, and immunity which are mixed in the body fluid.

The chemical sensor $13i$ changes in electric property or optical property by adhering the body fluid to the sensor surface.

The chemical sensor for analyzing (sensing) the structure of arrangement of protein or specific gene uses a square-plate sensor comprising an electrode array, serving as a sensor surface, having several tens to thousands gold electrodes with the size of $\phi 40\mu$. The bottom side of the electrode array comprises a substrate having a large number of terminals for external connection.

According to the first embodiment, a recovery device of the chemical sensor comprises sensor surface recovery means which recoveries the same sensor surface or sensor surface switching means which switches the sensor surface, thereby enabling the continuous sensing operation.

Referring to FIG. 2C, the chemical sensor $13i$ is connected to a sensing circuit 14. The sensing circuit 14 performs the signal processing of an output signal of the chemical sensor $13i$, thereby sensing whether or not the examination target exists and the amount of examination target when exists, based on the change in output signal sensed by the chemical sensor $13i$.

The output signal of the sensing circuit 14 is sent to a control circuit 15. The control circuit 15 controls the operation of the sensing circuit 14, performs the signal processing, such as A/D conversion, of the output signal of the sensing circuit 14, and sends the processed signal to a radio circuit 16.

The radio circuit 16 modulates sensing information sensed by the chemical sensor $13i$ (and the sensing circuit 14) inputted from the control circuit 15, and extracorporeally sends the modulated information by radio waves via an antenna (coil) 17. The extracorporeal device 4 that is extracorporeally arranged receives the radio waves, and the sensing information sensed by the chemical sensor $13i$ is stored in a memory in the extracorporeal device 4.

Referring to FIG. 1, the patient 2 swallows the capsule medical device 3, thereby sending, by radio waves, the sensing information sensed by the chemical sensor $13i$. The extracorporeal device 4 receives the sensing information by the antenna 6, demodulates the received information by the radio circuit therein, adds the receiving time to the sensing information demodulated, and stores the receiving time and the sensing information to the memory such as a semiconductor memory (not shown).

According to the first embodiment, the capsule medical device 3 comprises recovery means which resets the chemical sensor $13i$ substantially to the initial state and periodically performs the recovery processing so that the capsule medical device 3 can continuously examine the examination target in the body (specifically, at least a plurality of times or almost continuously) by the chemical sensor $13i$ provided for the capsule medical device 3 for a long time (till extracorporeally evacuating the capsule medical device 3, namely, for 3 to 8 hours).

Referring to FIG. 2C, the capsule medical device 3 according to the first embodiment comprises a heater $18i$ for heating operation on the rear surface of the chemical sensor $13i$. The heater $18i$ is connected to a heater circuit 19. The heater $18i$ heats the chemical sensor $13i$ by receiving a driving signal (driving power) from the heater circuit 19, thereby drying the sensor surface.

Further, the capsule medical device 3 comprises a battery 20 which feeds power for operation to the heater circuit 19, the sensing circuit 14, the control circuit 15, and the radio circuit 16.

As mentioned above, according to the first embodiment, the chemical sensor $13i$ is always exposed to the body fluid. Therefore, undesired substances such as the body fluid in the previous state or mucosa are adhered or are stagnated to the sensor surface. The sensing property shifts from the sensing property in the initial state, and deteriorates. Thus, the recovery means resets the chemical sensor $13i$ to the initial state by heating the sensor surface by the heater $18i$.

That is, since the surface of the chemical sensor $13i$ is always exposed to the body fluid, the mucosa might be adhered to the surface of the chemical sensor $13i$. Thus, the chemical sensor $13i$ might not function in the initial state due to the adhesion of mucosa. However, the recovery processing for recovering the sensor surface of the chemical sensor $13i$ is executed in such a manner that the chemical sensor $13i$ is periodically heated by the heater $18i$ arranged to the rear of the chemical sensor $13i$, the sensor surface of the chemical sensor $13i$ is dried, and the undesired substances adhered are cleared.

The control circuit 15 controls the periodical heating operation of the heater $18i$ via the heater circuit 19.

Next, a description is given of the operation of the capsule medical device 3 with the above-mentioned structure.

Referring to FIG. 1, the capsule medical device 3 is swallowed by the patient 2. Then, the sensing information is always obtained by performing the signal processing of the output from the chemical sensor $13i$ by the sensing circuit 14, and the obtained information is extracorporeally sent by the radio waves via the radio circuit 16 and the antenna 17. The extracorporeal device 4 receives the radio waves by the antenna 6, and further stores, by using the demodulating circuit, the sensing signal sensed by the chemical sensor $13i$ and the sensing circuit 14 to the memory such as a non-volatile memory together with the information on the receiving time.

The capsule medical device 3 exists in the body for 5 to 12 hours from the time for swallowing the capsule medical device 3 to the time for evacuating it. The capsule medical device 3 sequentially passes through the gastrointestinal tracts such as esophagus, stomach, small intestine, and large intestine, and is evacuated from the anus. When the capsule medical device 3 passes through the gastrointestinal tracts, the sensor surface serving as the sensing surface of the chemical sensor 13*i* of the capsule medical device 3 is always exposed to the body fluid and therefore the undesired substances such as mucosa might be adhered.

In this case, the sensing function might deteriorate on the sensor surface of the chemical sensor 13*i*. However, according to the first embodiment, the heater 18*i* periodically heats the back (bottom) of the chemical sensor 13*i*, the sensor surface of the chemical sensor 13*i* is dried, or the undesired substances adhered to the sensor surface are cleared or burnt out, thus maintaining the initial sensing characteristics by restoring the sensor surface to the initial state.

Since the chemical sensor 13*i* is periodically reset and is recovered, the sensing operation continues without deteriorating the sensing performance.

According to the first embodiment, since the chemical sensor 13*i* is periodically heated to the recovery operation, the sensing operation continues. That is, the chemical sensor 13*i* enables the sensor devices to be used continuously or a plurality of times.

Furthermore, according to the first embodiment, the sensing data without deterioration of sensing property is obtained for accurate diagnosis.

Figure 3:
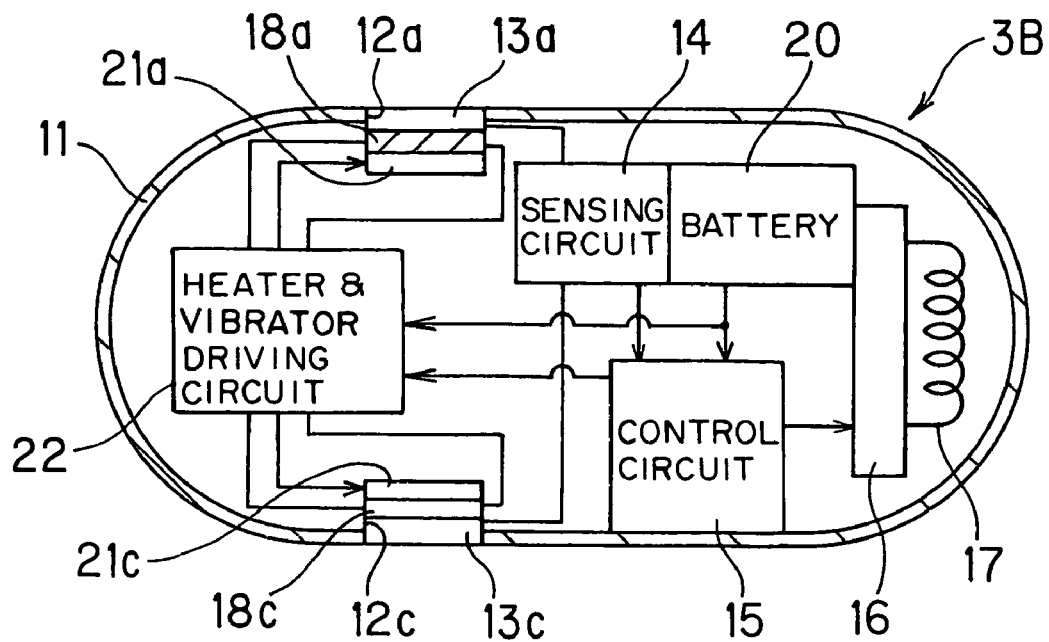
FIG. 3 is a diagram schematically showing the internal structure of a capsule medical device according to a first modification.

FIG. 3 shows a capsule medical device 3B according to a first modification. The capsule medical device 3B is formed by attaching a vibrator 21*i* comprising a piezoelectric element to the back of the heater 18*i*. In place of the heater circuit 19, a heater and vibrator driving circuit 22 is used to drive the heater 18*i* and the vibrator 21*i*.

The control circuit 15 controls the heater and vibrator driving circuit 22 and, consequently, the heater 18*i* dries the chemical sensor 13*i*. Further, the vibrator 21*i* is vibrated, thereby removing the adhesion onto the chemical sensor 13*i* to recover or set the chemical sensor 13*i* to the initial state.

An AC driving signal (or signal with a rectangular wave, or triangular wave) is applied to the vibrator 21*i* from the heater and vibrator driving circuit 22 under the control of the control circuit 15. Then, the vibrator 21*i* is vibrated in the direction in parallel with the sensor surface of the chemical sensor 13*i*. Upon periodically driving the heater 18*i* or vibrator 21*i*, both the heater 18*i* and the vibrator 21*i* may be simultaneously driven. Further, after drying the sensor surface by driving the heater 18*i*, the vibrator 21*i* is driven and then the vibration efficiently removes the remaining undesired substances due to the drying operation or burning operation on the sensor surface. Other structures are the same as those according to the first embodiment.

According to the first modification, the vibrator 21*i* is operated, thereby efficiently removing the undesired substances adhered to the chemical sensor 13*i*.

Figure 4:
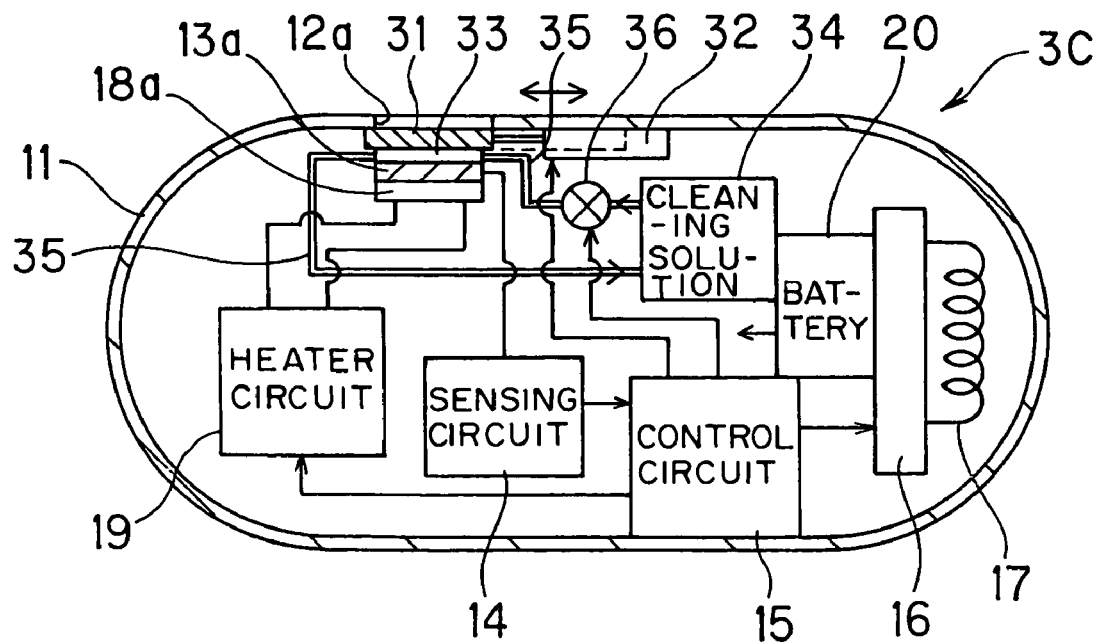
FIG. 4 is a diagram schematically showing the internal structure of a capsule medical device according to a second modification.

FIG. 4 shows a capsule medical device 3C according to a second modification. The capsule medical device 3C is structured by arranging a cover 31 slidable in the longitudinal direction in the opening 12*i* (i=a in FIG. 4) and by moving the cover 31 in the longitudinal direction of the capsule medical device 3C as shown by an arrow in FIG. 4 by a cover moving mechanism (cover opening/closing mechanism) 32 to open/close the opening 12*i*.

The sensor surface of the chemical sensor 13*i* (facing the opening 12*a*) is arranged to be directed to the top via cleaning space 33 arranged in the cover 31.

Similarly to the case shown in FIG. 2C, the heater 18*i* is attached to the back of the chemical sensor 13*i*.

The capsule medical device 3C according to the second modification comprises a chamber 34 for cleaning solution for accommodating a cleaning solution. The chamber 34 for cleaning solution is connected to a cleaning space 33 via two tubes 35 for circulating the cleaning solution, and a pump 36 for feed/suction of solution is inserted in the halfway of one tube 35.

The control circuit 15 controls the driving operation of the pump 36. Further, the control circuit 15 controls the operation of the cover moving mechanism 32.

Other structures are the same as those of the capsule medical device 3B shown in FIG. 2C. Although one chemical sensor 13*a* is shown for a brief description in FIG. 4, the same structure may be used for the arrangement positions of other chemical sensors 13*b* to 13*d*.

Figure 5:
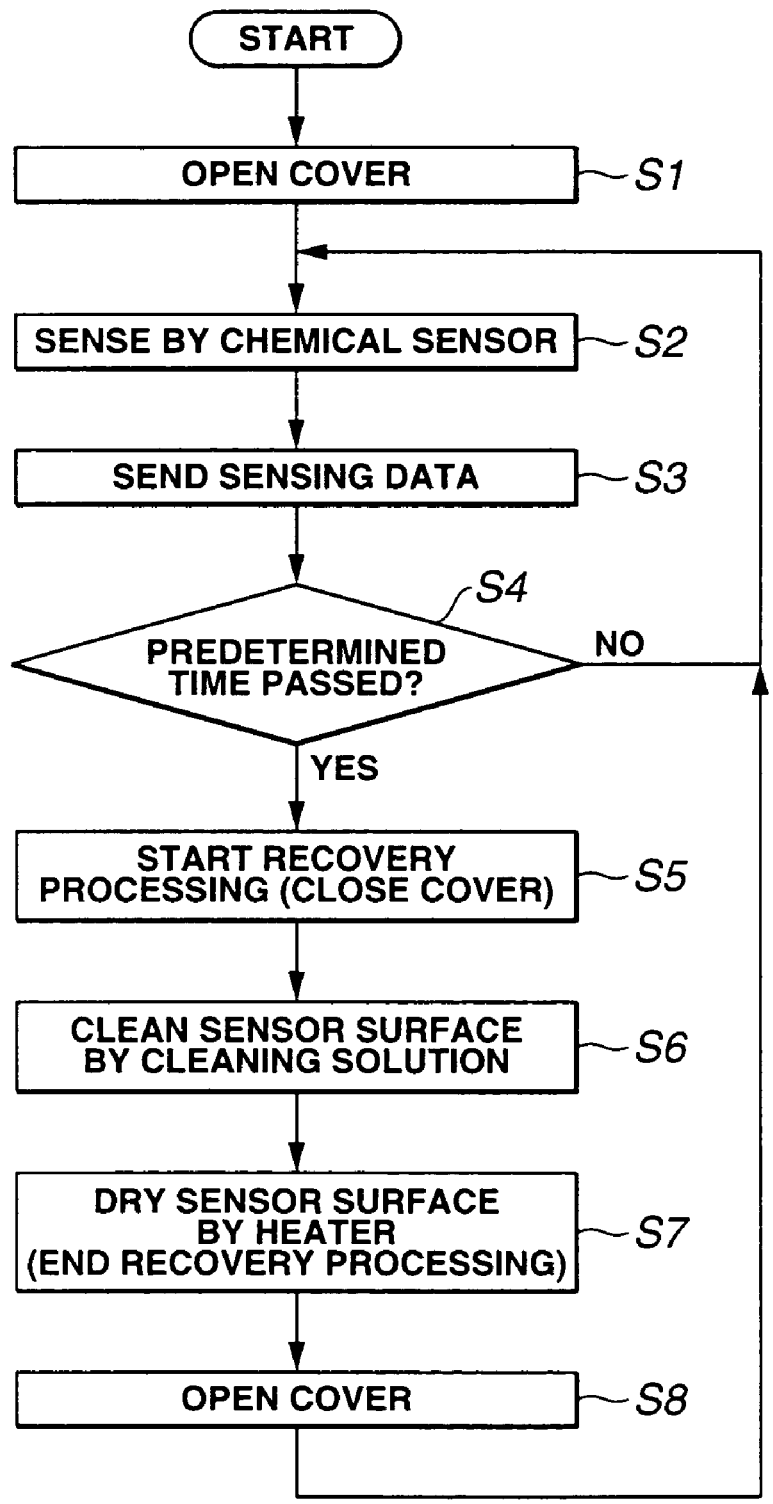
FIG. 5 is a flowchart showing the operation contents according to the second modification.

According to the first embodiment, in the case of sensing operation using the chemical sensor 13*a*, referring to FIG. 5, the sensing property is recovered and the sensing operation is repeated by periodical recovery processing. The recovery processing is riot limited to the periodical one (at the interval of a predetermined time) and may be performed at a proper time interval.

In step S1, the control circuit 15 sends the control signal to the cover moving mechanism 32, the cover moving mechanism 32 moves the cover 31, and thus the cover 31 that closes the opening 12*a* is opened.

By opening the cover 31, the sensor surface of the chemical sensor 13*a* is exposed to the opening 12*a*. In step S2, the chemical sensor 13*a* performs the sensing operation.

Sensing data which is sensed by the chemical sensor 13*a* and is obtained by sensing the target via the sensing circuit 14 is sent from the antenna 17 as shown in step S3. Further, the sensing data is received by the extracorporeal device 4 and is stored in the extracorporeal device 4.

In step S4, the control circuit 15 determines whether or not a predetermined time passed after starting the sensing operation. If it is determined that the predetermined time does not pass, the processing returns to step S2. On the other hand, if it is determined that the predetermined time passes, in step S5, the control circuit 15 executes the restoring processing as follows.

That is, the control circuit 15 stops the sensing operation using the chemical sensor 13*a* which executes the sensing operation for a predetermined time, and closes the opening 12*a* that the chemical sensor 13*a* faces by driving the cover moving mechanism 32 to move the cover 31.

In step S6, the control circuit 15 drives the pump 36 to flow (feed) the cleaning solution to the cleaning space 33 that the sensor surface faces, and cleans the sensor surface. The cleaning solution cyclically flows, passing through the sensor surface, thereby cleaning the sensor surface to recover the clean state.

In step S7, the control circuit 15 drives the heater 18*a* via the heater circuit 19 to heat the chemical sensor 13*a* and to dry the sensor surface. Then, the recovery processing ends.

In step S8, the control circuit 15 opens, via the cover moving mechanism 32, the cover 31 which covers the sensor surface of the chemical sensor 13*a* that is recovered.

Then, the processing returns to step S2 whereupon the chemical sensor 13*a* performs the sensing operation.

By alternately performing the sensing operation and the recovery processing at the predetermined time interval, the recovery processing is performed after the sensing operation by the chemical sensor 13*a*. Then, the chemical sensor 13*a* is reset to the initial state. The chemical sensor 13*a* that is recovered to the clean state repeats the sensing operation.

According to the second modification, the chemical sensor 13*i* is cleaned by the cleaning solution before drying the chemical sensor 13*i* by the heater 18*i*. Therefore, the sensor surface is reliably recovered to the clean state.

Incidentally, as a modified one of the second modification, the simplified structure may be used by the structure excluding the cover 31.

Further, the cover 31 and the cover moving mechanism 32 may be arranged without the recovery structure by the cleaning operation using the cleaning solution. That is, in the recovery processing, the chemical sensor 13i is efficiently dried by closing the opening 12i of the chemical sensor 13i for recovery processing with the cover 31.

Although the second modification uses the first embodiment, it may use the first modification. In this case, as mentioned above, the cover 31 and the cover moving mechanism 32 may be arranged. That is, in the recovery processing, the chemical sensor 13i is efficiently dried by closing the opening 12i of the chemical sensor 13i for recovery processing with the cover 31. Further, the vibrator 21i vibrates the chemical sensor 13i, thereby efficiently removing undesired substances.

Figure 6:
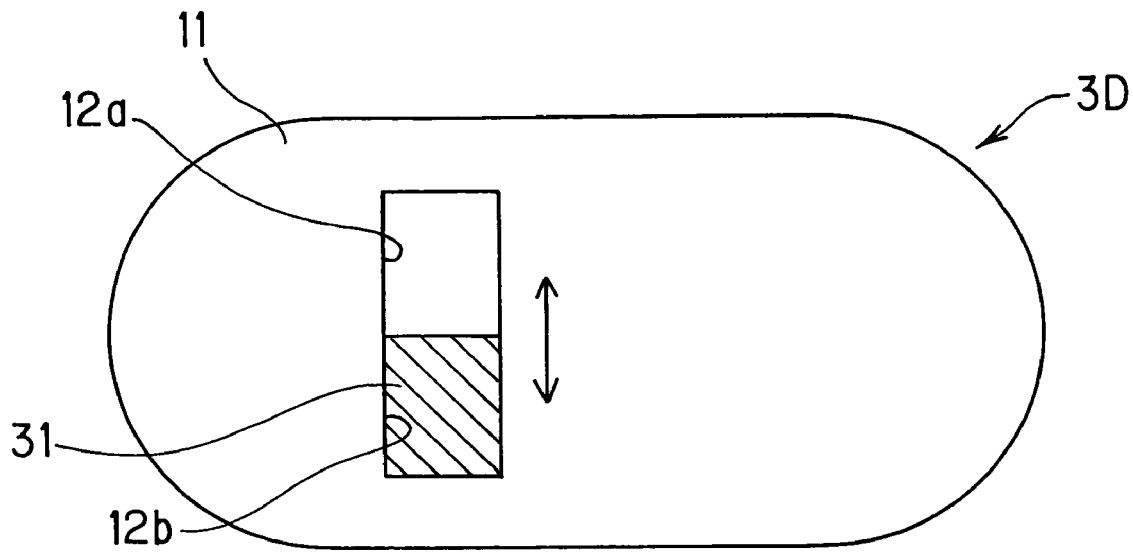
FIG. 6 is a plan view showing a capsule medical device according to a third modification.

FIG. 6 shows a capsule medical device 3D according to the third modification. The capsule medical device 3D according to the third modification is obtained by arranging two chemical sensors adjacently thereto and alternately opening the cover 31 in the capsule medical device 3C shown in FIG. 4. In this case, the cover 31 functions as sensor surface switching means.

Referring to FIG. 6, the openings 12a and 12b are arranged adjacently thereto in the circumferential direction of the capsule medical device 3D. Inside the openings 12a and 12b, the cover 31 is arranged and the cover 31 can be moved in the circumferential direction by the cover moving mechanism 32 that is not shown in FIG. 6.

A chemical sensor 13j on the sensor surface opened at an opening 12j (j=a or b) at which the cover 31 is opened performs the sensing operation. Meanwhile, the chemical sensor closed by the cover 31 performs the recovery processing.

According to the third modification, continuously, one of the two adjacently-arranged chemical sensors 13a and 13b performs the sensing operation and the other performs the recovery processing. Therefore, the two chemical sensors 13a and 13b always measures the data. That is, if one of the two chemical sensors is in the progress of the recovery processing, the other chemical sensor 13j performs the sensing operation.

If the two chemical sensors 13a and 13b are the same ones, the sensing operation is always executed. The time for interrupt of the sensing operation is substantially solved. Further, in place of the two chemical sensors 13a and 13b, the one chemical sensor 13a may be arranged to cover the openings 12a and 12b.

Figure 7:
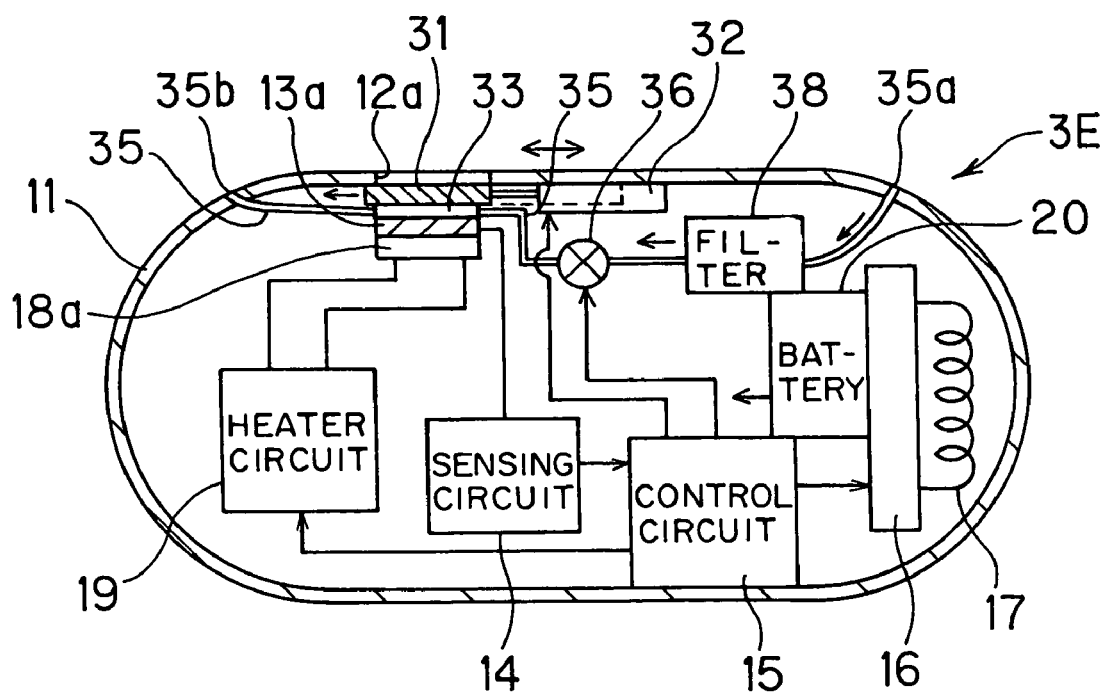
FIG. 7 is a diagram schematically showing the internal structure of a capsule medical device according to a fourth modification.

FIG. 7 shows a capsule medical device 3E according to the fourth modification. The capsule medical device 3E is structured by using the digestive fluid in the body for cleaning operation without the included the cleaning solution.

Therefore, the capsule medical device 3E is structured by externally connecting an end of the one tube 35 connected to the pump 36 to the exterior case 11 via a filter 38 as cleaning solution cleaning means which is inserted in the halfway without the connection to the chamber 34 for cleaning solution in the capsule medical device 3C shown in FIG. 4. The end becomes a suction port 35a.

An end of the other tube 35 is not connected to the chamber 34 for cleaning solution, but is externally connected to the exterior case 11. The end becomes a drain port 35b. Other structures are the same as those of the capsule medical device 3C shown in FIG. 4.

In the cleaning operation according to the fourth modification, the body fluid is sucked by the pump 36 through the suction port 35a, the filter 38 executes the filtering processing to obtain the clear cleaning solution, the cleaning solution flows to the cleaning space 33 arranged to the sensor surface, and the solution used for cleaning operation is externally discharged outside the capsule medical device 3E through the drain port 35b.

The cleaning function is the same as that in case of including the cleaning solution as shown in FIG. 4.

According to the fourth modification, the same operations and advantages as those shown in FIG. 4 are obtained. The cleaning solution does not need to be accommodated in the capsule medical device 3E. Therefore, the capsule medical device reduces the size. Since the amount of solution necessary for cleaning operation does not need to be accommodated in, the costs are reduced.

A sensing output of the chemical sensor 13i during the cleaning operation by the body fluid via the filter 38 may be a reference output, thereby correcting the output of the chemical sensor 13i for each sensing portion. As a consequence, the sensing operation is executed with high precision.

Second Embodiment

Figure 8:
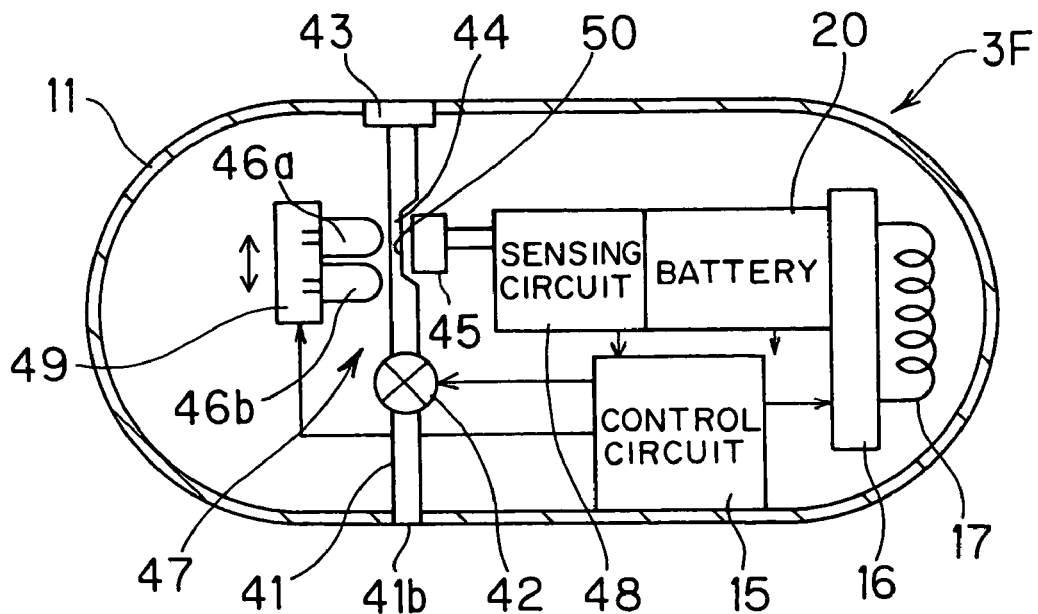
FIG. 8 is a diagram schematically showing the internal structure of a capsule medical device according to a second embodiment of the present invention.

Next, a second embodiment of the present invention will be described with reference to FIG. 8. According to the second embodiment, the same components as those according to the first embodiment are designated by the same reference numerals and a description thereof is omitted. FIG. 8 shows a capsule medical device 3F according to the second embodiment. According to the second embodiment, unlike the first embodiment, an optical chemical sensor is provided for sensing the component from the optical property of, e.g., the body fluid.

Referring to FIG. 8, the capsule medical device 3F of the second embodiment comprises: a transparent glass tube 41 across the exterior case 11; and a pump 42 for feed/suction of solution which is inserted in the halfway of the glass tube 41. One opening end of the pump 42 sucks the body fluid and the other opening end discharges it. That is, one opening end of the glass tube 41 becomes a suction port and the other opening end of the glass tube 41 becomes a drain port 41b.

A filter 43 is arranged at the opening end serving as the suction port so as to prevent the flow of the solid in the glass tube 41.

An optical window portion 44 which is narrowed as a thin and flat tube for optical sensing operation is arranged in the halfway of the glass tube 41. An optical sensor 45 is arranged, facing the optical window portion 44. An (optical) sensing unit 47 is formed so that a light-emitting element 46a can be arranged, facing the optical sensor 45, to sandwich the optical window portion 44.

The light-emitting element 46a comprises a blue light-emitting device such as a blue laser diode or a blue LED which emits blue light with the wavelength of approximately 415 nm indicating the unique absorption property of the hemoglobin in the blood, irradiates the blue wavelength light to the optical window portion 44, and senses the amount of light by the optical sensor 45 via the glass tube 41 in the optical window portion 44 and the body fluid in the optical window portion 44.

The narrow optical window portion 44 senses the amount of transmission light, thereby increasing the sensing area of the light and making the lengths of optical paths in the portions uniform. That is, the optical sensing unit 47 optimizes the length of optical paths.

The optical sensor 45 inputs the sensing signal to a sensing circuit 48. The sensing circuit 48 compares the input data with a reference level corresponding to the normal transmission-intensity without the hemoglobin, amplifies a difference signal, and sends it to the control circuit 15. The output of the sensing circuit 48 becomes the sensing signal corresponding to the amount of hemoglobin when it is determined whether or not the hemoglobin is included and then it is determined that it is included.

According to the second embodiment, means for recovering or resetting the sensing unit 47 as follows is provided.

That is, a light-emitting element 46b is arranged. The light-emitting element 46b comprises an ultraviolet LED which emits ultraviolet light or an LD for ultraviolet light-emission, adjacently to the light-emitting element 46a. Specifically, the light-emitting element 46b adjacent to a light-emitting element 46a is attached to a moving mechanism 49, thereby moving the light-emitting element 46b near the optical window portion 44 forming the sensing unit 47.

A photocatalyst film (or photocatalyst coating portion) 50 is formed to the inner surface of the optical window portion 44. The ultraviolet-light irradiation activates the photocatalyst film 50, thereby having a function for cleaning the dirt adhered to the inner surface of the glass tube 41 and a function for preventing the adhesion of dirt.

In the case of performing sensing operation using the light-emitting element 46a for a predetermined time, the moving mechanism 49 moves the light-emitting element 46b under the control of the control circuit 15, the light-emitting element 46b irradiates the ultraviolet light to the glass tube 41 near the sensing unit 47. The photocatalyst film 50 resets, to the clean state, the inner surface of the glass tube 41 near the sensing unit 47. Alternatively, the light-emitting element 46b may emit the light in the state without the moving mechanism 49. In this case, the structure is simplified.

Other structures are the same as those according to the first embodiment.

According to the second embodiment, the hemoglobin in the blood absorbs the largest amount of light with the wavelength of 415 nm. When the blood is mixed in the body fluid (bleeding in the gastrointestinal tract), the amount of light reaching the optical sensor 45 is extremely small. The change enables the sensing operation of blood.

Since the glass tube 41 forming the sensing unit 47 is cleaned by using the photocatalyst, the sensing performance does not deteriorate.

According to one modification of the second embodiment, in place of using the light-emitting element 46a, a multi-light-emitting element may be structured by forming one light-emitting element, as a multi-light-emitting element, having the function of the light-emitting element 46a and a function of another light-emitting element for emitting light with the wavelength having not the unique absorbing property of the hemoglobin. The optical sensor 45 senses both the transmission light in the one light-emitting element for emitting the blue light and the transmission light in the other light-emitting element for emitting the light. A value of the transmission light of the other light-emitting element may be used as a reference one, and the hemoglobin in the blood, namely, the blood may be sensed from the amount of attenuation (compared with the reference value) of the intensity of the transmission light from the obtained value. Further, the optical property of the body fluid component other than the hemoglobin may be used to sense the component in accordance with the application.

Alternatively, according to the embodiment with reference to FIG. 8, the light-emitting element 46a and the light-emitting element 46b may be a multi-light-emitting element. Then, the moving mechanism 49 is not necessary, and the size is reduced. Or, according to the embodiment, the light may be irradiated in the living body and return light from the body fluid or surface of the inner wall in the body cavity or scattering light may be sensed, unlike the sensing operation of the transmission light according to the embodiment.

Figure 9:
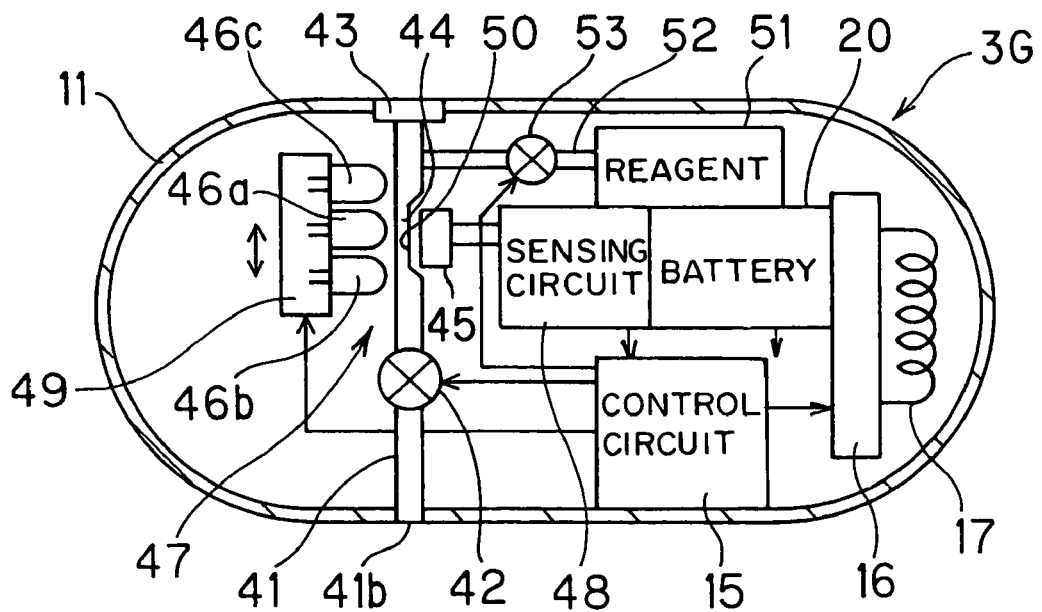
FIG. 9 is a diagram schematically showing the internal structure of a capsule medical device according to a first modification.

FIG. 9 shows a capsule medical device 3G according to the first modification. The capsule medical device 3G has a function for sensing another component in addition to the function for sensing the hemoglobin in the blood in the capsule medical device 3F shown in FIG. 8.

Specifically, the capsule medical device 3G includes a reagent accommodating unit 51 including a reagent for coloring the substance in reaction to the examination target in the body fluid, and is connected to the glass tube 41 via a tube 52. Further, a pump 53 is arranged in the halfway of the tube 52, and the control circuit 15 controls the driving operation of the pump 53 to feed the reagent to the glass tube 41 side and mix (drop) the reagent in the body fluid.

By dropping the reagent in the body fluid, the reagent is reacted to the examination target such as protein, carbohydrate, lipid, drug, enzyme, gene, and immunity which are mixed in the body fluid, thereby being converted into the pigment. By using the absorption of the converted pigment, the amount or concentration of the examination target is sensed. Further, a pH level is sensed by using the reagent for showing the pH in the body fluid as color change.

A white LED 46c for emitting white light is attached to the moving mechanism 49. Other structures are the same as those shown in FIG. 8.

According to the first modification, the operations of the light-emitting element 46a and the light-emitting element 46b are the same as those according to a seventh embodiment. Further, in the case of sensing another examination target, the control circuit 15 controls the moving mechanism 49 so that the white LED 46c faces the optical window portion 44. Furthermore, the white LED 46c emits the light and the optical sensor 45 senses the amount of transmission light via the optical window portion 44, thereby sensing the amount or concentration of the examination target.

According to the first modification, another examination target can be sensed, in addition to the sensing operation of the blood.

According to another modification, the inner surface of the portion except for the sensing unit 47 of the glass tube 41 is subjected to MPC polymer coating.

The MPC polymer coating which prevents the adhesion of protein has the advantage for preventing the dirt, though the effect is lower than that of the photocatalyst. However it does not need the irradiation of ultraviolet light. Incidentally, the MPC polymer is the abbreviation of 2-Methacryloyl-oxy-ethyl phosphorylcholine polymer, and is obtained by partly replacing the polymer structure with the same structure as that of phospholipids forming the biomembrane.

According to the modification, the glass tube 41 for optical sensing operation is easily kept to be clean.

Third Embodiment

Figure 10:
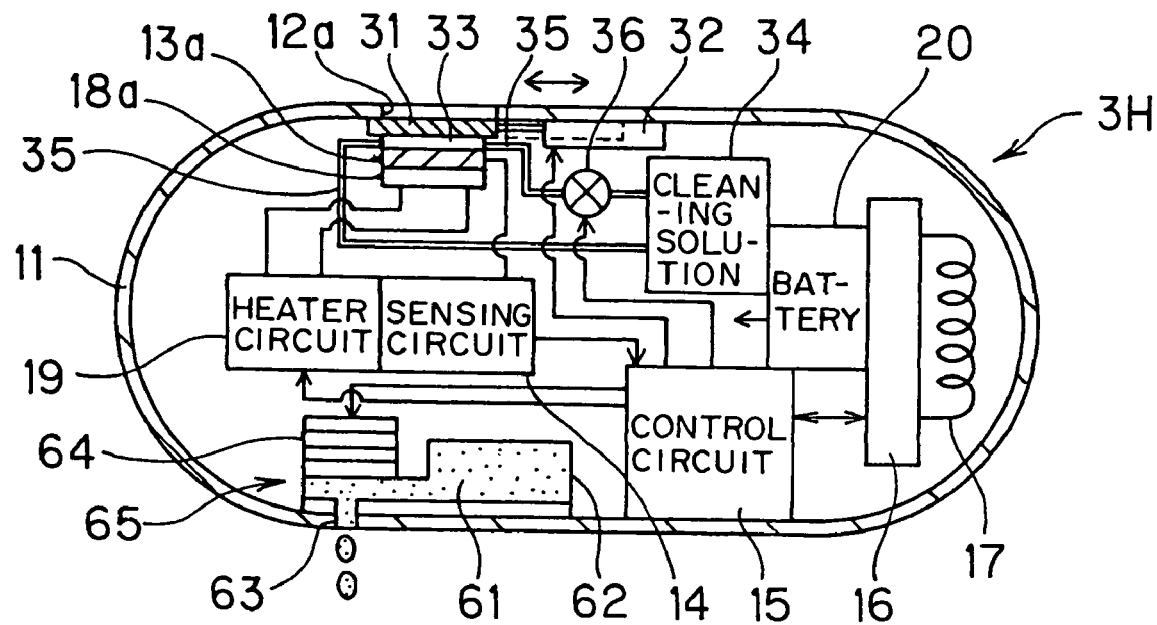
FIG. 10 is a diagram schematically showing the internal structure of a capsule medical device according to a third embodiment of the present invention.

Next, a description is given of a third embodiment of the present invention with reference to FIG. 10. FIG. 10 shows a capsule medical device 3H according to the third embodiment of the present invention. According to the third embodiment, the capsule medical device 3H is structured by arranging a marking function (marker function) which places a marker to a sensed portion in accordance with the sensing result so as to easily correspond to the later precise examination of the examination target that is sensed by the chemical sensor 13i in the capsule medical device 3C shown in FIG. 4 according to the second embodiment.

Therefore, the capsule medical device 3H is structured by further arranging an accommodating tank 62 of a marking agent 61 and a small nozzle 63 arranged to the accommodating tank 62, which is externally opened to the exterior case 11 in the capsule medical device 3C.

The accommodating tank 62 comprises: a piezoelectric element 64 on the facing side of the nozzle 63; and a marking mechanism 65 for adhering the small mass of the marking agent 61 near the portion (examination target at the level higher than the normal state) sensed by the chemical sensor 13a and adhering the marking by driving the piezoelectric element 64 by the control circuit 15 and by discharging (or ejecting) the marking agent 61 in the accommodating tank 62 from the nozzle 63 by the ink-jet system.

Simply, the marking agent 61 is a stain of a black marker for gastrointestinal tract (such as SPOT produced by GISupply, U.S.). Further, the marking agent 61 may be living body adherent polymer, a magnetic member, or another member. Since the living body adherent polymer has a property of adhesion to the cell in the gastrointestinal tract, the colored polymer may be used as a marker. Furthermore, a minute needle may be picked-up from the capsule medical device and the marking agent may be injected to the organ without discharging the marking agent.

According to the third embodiment, the radio circuit 16 has a receiving function as well as the sending function for sending the received signal to the control circuit 15. The control circuit 15 controls the marking mechanism 65 by a signal inputted from the radio circuit 16.

Figure 11:
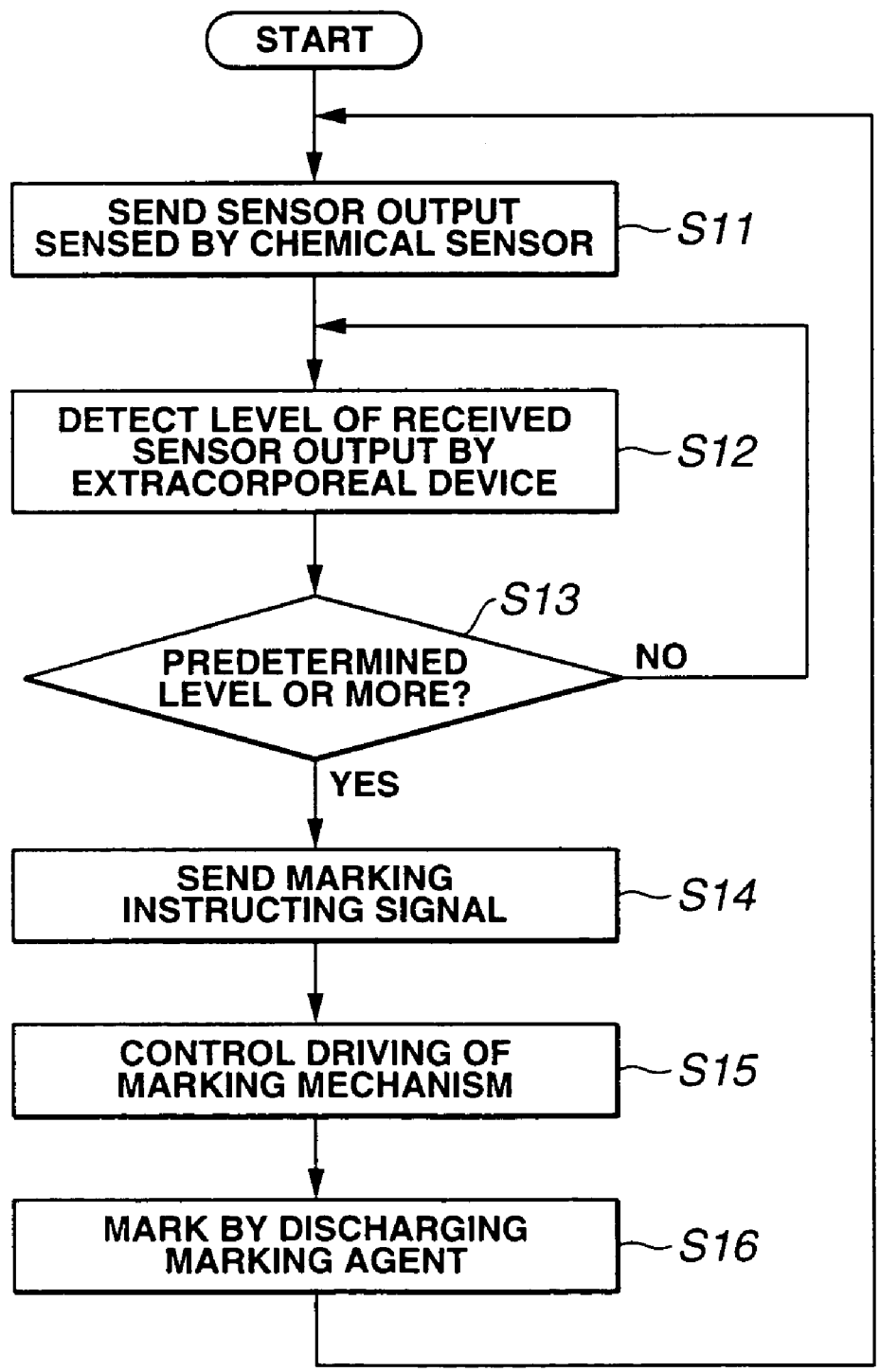
FIG. 11 is a flowchart showing the operation contents according to the third embodiment.

Next, the operation according to the third embodiment will be described with reference to FIG. 11.

The patient 2 swallows the capsule medical device 3H, and the capsule medical device 3H is sent to the gastrointestinal tract in the body cavity.

In step S11, the chemical sensor 13i and the sensing circuit 14 incorporated in the capsule medical device 3H sense the target as mentioned above with reference to FIG. 4, and the sensed sensor output (sensing data) is extracorporeally sent by radio waves.

In step S12, (the CPU not shown in) the extracorporeal device 4 detects the level of the received sensor output. In step S13, it is determined whether or not the sensed level is a predetermined level, which is over the normal range, or more.

If it is determined that the level is not a predetermined level or more, the processing returns to step S12. On the other hand, if it is determined that the sensed level is a predetermined level or more and the bleeding, tumor, or enzyme is sensed, in step S14, (the CPU in) the extracorporeal device 4 sends a marking instructing signal to the capsule medical device 3H.

In step S15, the capsule medical device 3H receives the marking instructing signal and the control circuit 15 controls for driving the marking mechanism 65. That is, the control circuit 15 drives the piezoelectric element 64 and thus the marking agent 61 is discharged form the nozzle 63 and the examination portion is marked. Then, the processing returns to step S11 whereupon the similar processing of the next sensor output is performed.

For the marked portion, the marker is sensed in the curing such as the medication by another capsule medical device or endoscope later. Consequently, the position such as the affected part for examination is specified promptly.

In addition to the advantages according to the second embodiment, advantageously, the sensed position of the abnormal portion (bleeding) in the body is easily sensed or specified to smooth the later treatment.

In the above description, the sensing data is extracorporeally sent and the marking instructing signal is generated on the side of the extracorporeal device 4. Further, the control circuit 15 in the capsule medical device 3H may determine whether or not the sensed level is a predetermined level or more and may control the operation for driving the marking mechanism 65 based on the determining result.

Figure 12A:
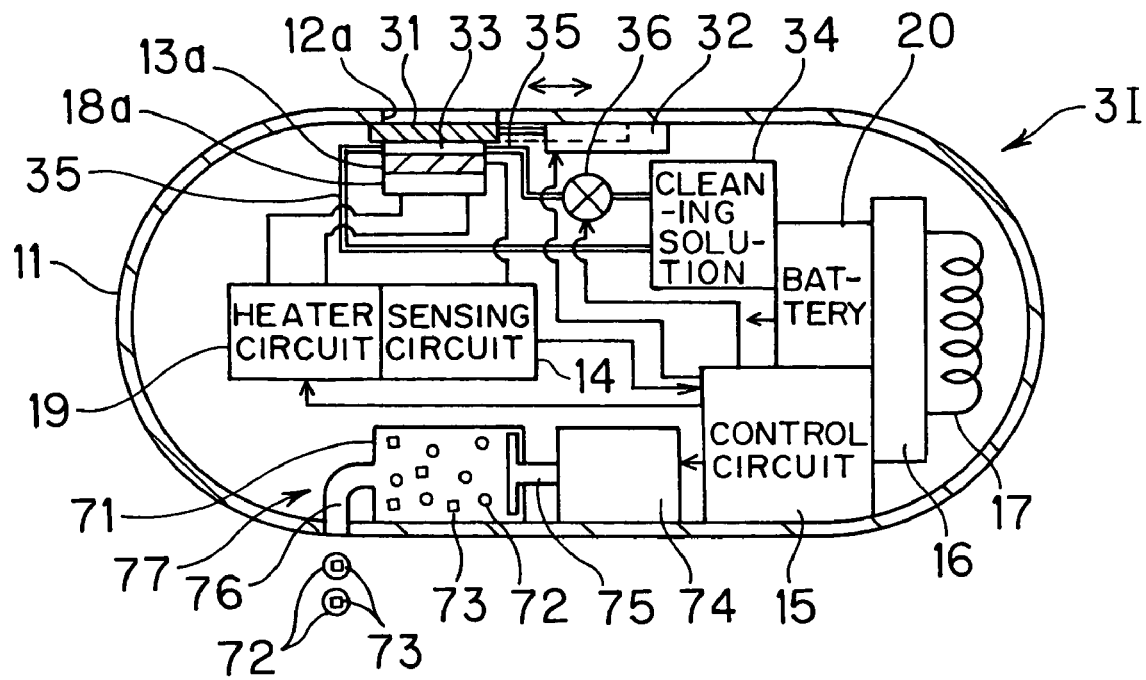
FIG. 12A is a longitudinal cross-sectional view showing the internal structure of a capsule medical device according to a first modification.

FIG. 12A shows a capsule medical device 3I according to a first modification. According to the first modification, the marking mechanism is different from that shown in FIG. 10.

The capsule medical device 3I mixedly accommodates therein a living body adherent polymer 72 and an RF-ID tag 73 for sending ID information by radio frequency (RF) in an accommodating tank 71. The RF-ID tag 73 comprises a minute tag (e.g., μ chip with 0.4 mm produced by Hitachi, Ltd.).

A movable piece 75 driven by a linear actuator 74 is fit into the accommodating tank 71. The capsule medical device 3I comprises a marking mechanism 77 which marks the examination target by moving the movable piece 75 and then by extracorporeally discharging the containing in the accommodating tank 71 from a nozzle 76.

In this case, the accommodating tank 71 mixedly accommodates the living body adherent polymer 72 and the RF-ID tag 73. Therefore, the living body adherent polymer 72 and the RF-ID tag 73 are discharged. Other structures are the same as those shown in FIG. 10.

Figure 12B:
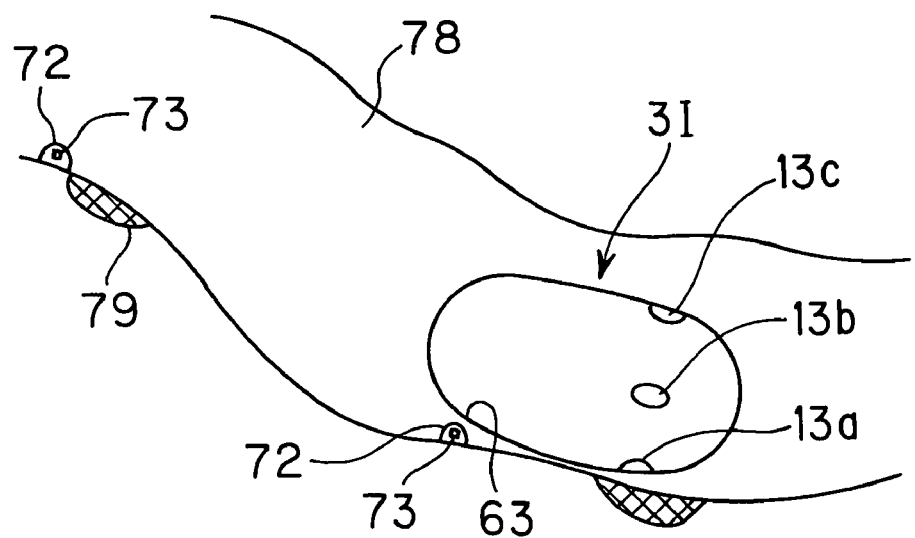
FIG. 12B is an explanatory diagram showing a using example.

FIG. 12B shows a using example according to the first modification. FIG. 12B shows the state of using the capsule medical device 3I in an intestine 78. When a bleeding portion 79 exists in the intestine 78 as shown by cross hatching, the chemical sensor 13a or the like senses it therenear at the high level. Then, as described above with reference to FIG. 11, the marking mechanism 77 is driven, and the living body adherent polymer 72 and the RF-ID tag 73 are discharged from the nozzle 76 and are adhered and fixed to the inner wall near the bleeding portion 79.

After the examination of the capsule medical device 3I, by external current scanning (radio sensing) using the RF-ID tag 73, the sensed radio signal enables the easy check of the marking position. In the operation or after the operation, the marking position is used in the medication by another capsule medical device.

According to the first modification, the sensed position is specified more assuredly.

FIG. 13A shows a capsule medical device 3J according to a second modification. Although the minute RF-ID tag 73 is used according to the first modification, a tube-shaped IC tag 81 is used according to the second modification. The IC tag 81 slightly increases in size as compared with that of the minute RF-ID tag 73. However, the sensing distance increases, the probability for extracorporeal sensing increases. Alternatively, the position is sensed with high precision.

The tube-shaped IC tag 81 includes an IC and an antenna coil in a resin tube or glass tube.

An IC tag accommodating unit 82 arranged in the capsule medical device 3J accommodates therein the tube-shaped IC tag 81 and the living body adherent polymer 72. Similarly to the case shown in FIG. 12A, the linear actuator 74 drives the IC tag 81 and the living body adherent polymer 72.

On the opposite side of a nozzle 83 of the IC tag accommodating unit 82, a solenoid 84 is arranged. The control circuit 15 drives the solenoid 84, thereby projecting and moving a movable piece of the solenoid 84. Then, the tube-shaped IC tag 81 is pressed out and the IC tag 81 in the covering state by the living body adherent polymer 72 is discharged from the nozzle 83.

Referring to FIG. 13A, the IC tag 81 is discharged in a gastrointestinal tract wall 86 and is fixed to the gastrointestinal tract wall 86.

As compared with the above-mentioned μ chip, the antenna is increased in size. The antenna increases in size, thereby reducing the radio frequency. The radio frequency is reduced and thus there are merits that the consumption energy is low and the passing through the living body is easy.

According to the second modification, the sensed position is specified more assuredly.

Referring to FIG. 13B, a capsule medical device 3K according to a third modification may comprise illuminating means and image pick-up means for capturing a living-body image. When the illuminating means and the image pick-up means are arranged, both the chemical sensing and the capturing of the living body image are simultaneously possible (or in parallel) to enable the more reliable diagnosis.

The capsule medical device 3K shown in FIG. 13B according to the third modification is structured by arranging a semi-spherical transparent cover 91 which seals one end of the exterior case 11 in the longitudinal direction thereof in the capsule medical device 3J shown in FIG. 13A. A lens frame 93 having an objective lens 92 is arranged near the center of the transparent cover 91. A CMOS imager 94 serving as the image pick-up means is arranged at the image forming position of the objective lens 92.

A light-emitting diode (hereinafter, abbreviated to an LED) 95 forming the illuminating means is attached to an LED substrate 96 having a driving circuit of the LED 95 around the lens frame 93.

The LED substrate 96 is arranged to the back of the CMOS imager 94 via a printed-circuit board 97, thereby driving the CMOS imager 94. Further, the LED substrate 96 is connected to a signal processing circuit substrate 98 for signal processing of the picked-up image signal.

The battery 20 supplies power necessary for operation to the signal processing circuit substrate 98 and the like. The signal processing circuit substrate 98 is electrically connected to the control circuit 15 and the radio circuit 16.

The LED 95 and the CMOS imager 94 emit (illuminate) light and pick up an image for a predetermined period. The control circuit 15 associates the sensing data from the chemical sensor 13a with the image data picked-up by the CMOS imager 94, and sends both the data to the extracorporeal device side from the antenna 17.

Referring to FIG. 13C, the control circuit 15 controls the operation for simultaneously sending image data Dg and the latest sensing data Dc at the obtaining timing of the image data Dg. Alternatively, the control circuit 15 may control the operation for simultaneously performing both the sensing and the capturing of the image.

The extracorporeal device 4 receives the image data Dg and the sensing data Dc sent from the capsule medical device 3K, then, stores both the data in association therewith in the memory in the extracorporeal device 4, adds the receiving time, and stores the data together with the receiving time.

According to the third modification, the control means of the image pick-up operation which controls the capturing means of the living body image is arranged, the sensing of the chemical sensor 13a and the image capturing are performed simultaneously or in conjunction therewith. The sensing of the chemical sensor 13a and the image capturing may be controlled in conjunction with the marking mechanism. Thus, the chemical information and the image information are associated therewith and are obtained to perform the more reliable diagnosis. Further, the sensed position is specified more assuredly.

Fourth Embodiment

A fourth embodiment of the present invention will be described with reference to FIGS. 14 to 17. FIG. 16A shows the internal structure of a capsule medical device. FIG. 16B shows a cross-sectional view of a line connecting A in FIG. 16A. FIG. 16C shows the structure of a sensor. FIG. 16D shows a driving signal of a motor. According to the fourth embodiment, sensor surface switching means for switching the sensor surface for sensing operation is formed as a recovery device of the chemical sensor as will be described later. Specifically, the sensor surfaces for sensing operation are sequentially changed.

Figure 14:
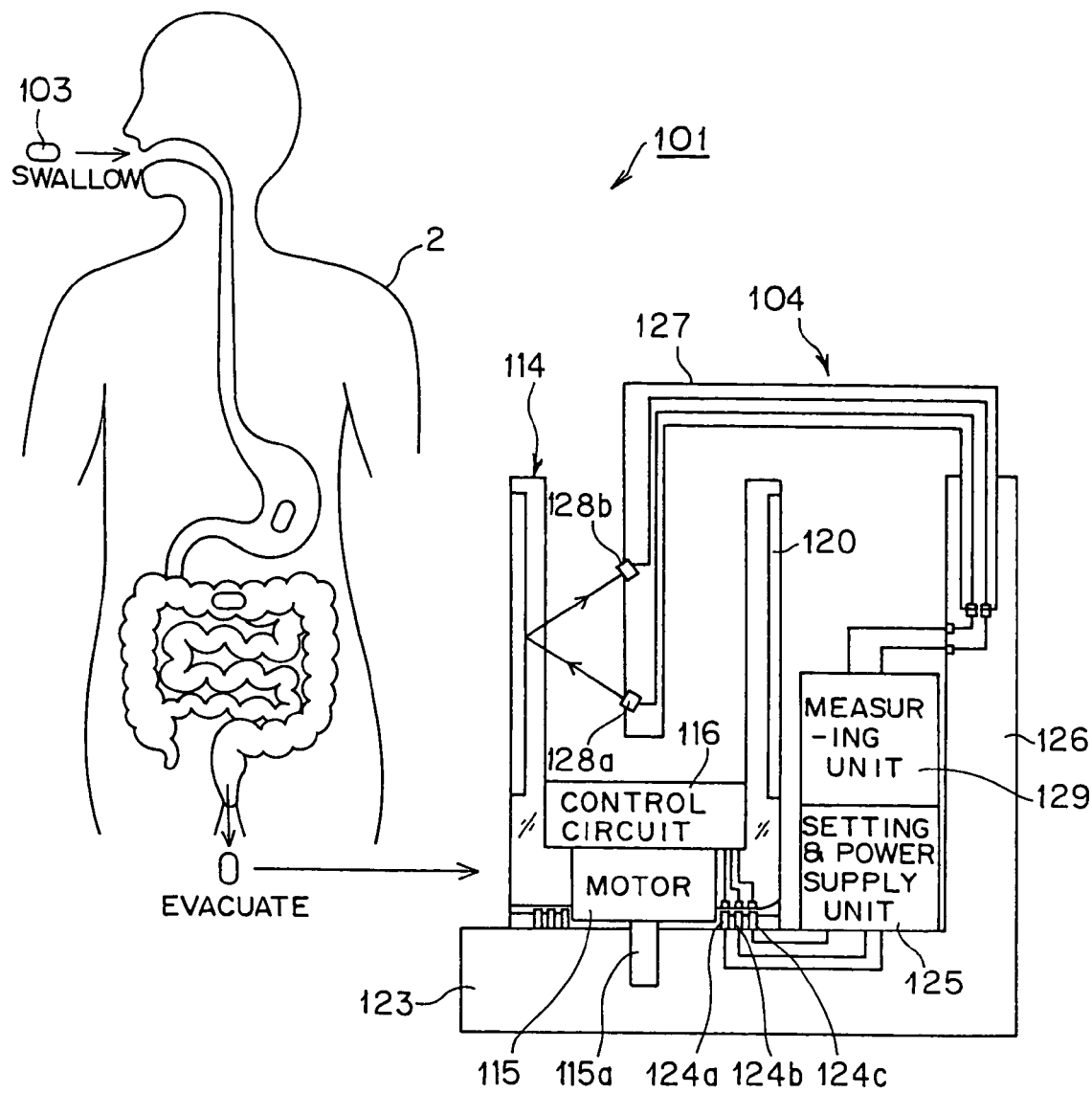
FIG. 14 is a diagram showing a capsule medical system according to a fourth embodiment of the present invention.

Referring to FIG. 14, a capsule medical system 101 comprises: a capsule medical device 103 according to the fourth embodiment which examines the body of the patient 2; and an analyzing device 104 which collects the capsule medical device 103 extracorporeally evacuated by the patient 2 and senses or analyzes the sensor information of the sensor surface from the sensor holder that holds the inner sensor.

Figure 15:
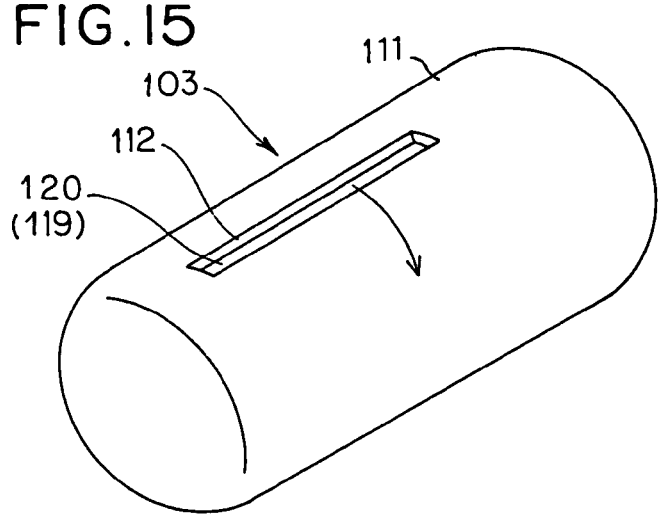
FIG. 15 is a perspective view showing the appearance of a capsule medical device according to the fourth embodiment of the present invention.
Figure 16A:
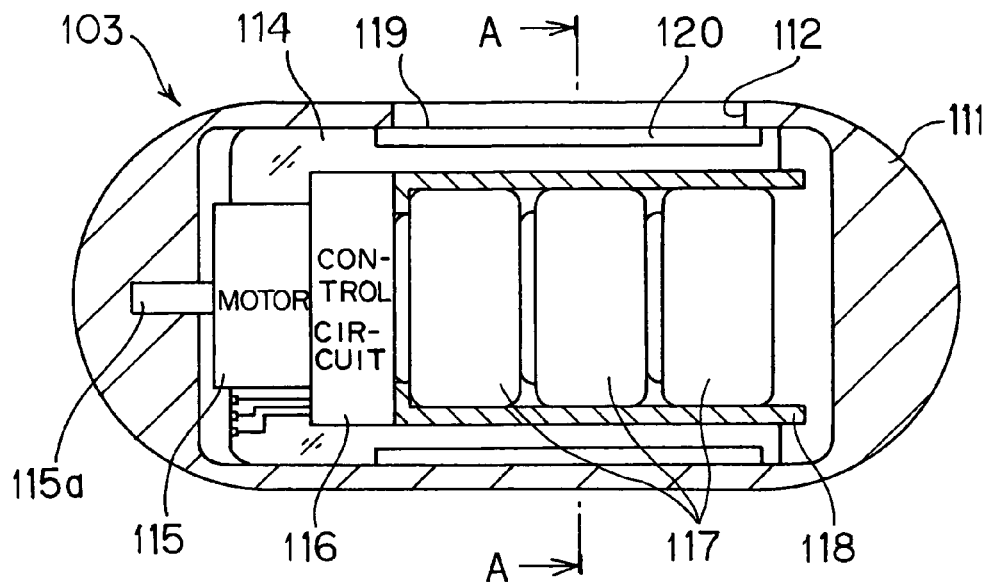
FIG. 16A is a longitudinal cross-sectional view showing the internal structure of the capsule medical device.
Figure 16B:
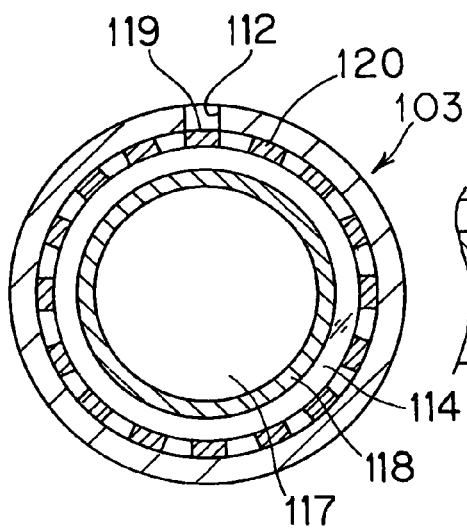
FIG. 16B is a cross-sectional view of a line connecting A in FIG. 16A.
Figure 16C:
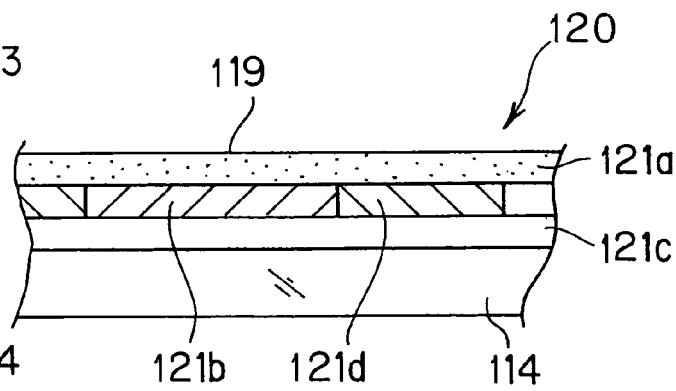
FIG. 16C is a cross-sectional view showing the structure of a sensor.
Figure 16D:
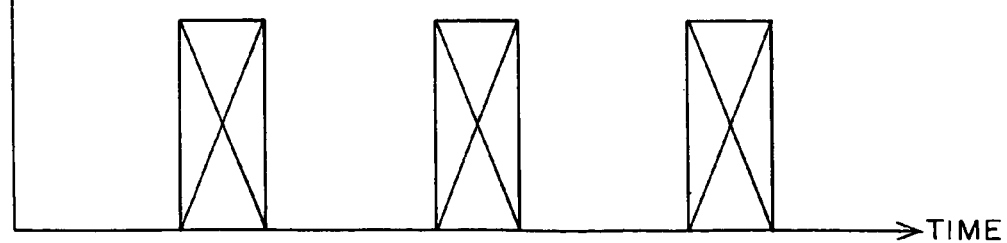
FIG. 16D is a diagram showing an example of a motor driving signal.

Referring to FIG. 15, the capsule medical device 103 comprises a capsule-shaped exterior case 111. The exterior case 11 comprises a slit-shaped opening 112 with the narrow width. A sensor 120 is held to a sensor holder 114 and is accommodated inside the opening 112.

As will be described with reference to FIG. 16A, the sensor holder 114 comprises a sensor surface exposing mechanism or a sensor surface exposure control mechanism which is rotated and moved relatively to the exterior case 111 and from which different sensor surfaces 119 of the sensor 120 facing the opening 112 are sequentially exposed on time series.

Referring to FIG. 16A, the cylindrically-shaped sensor holder 114 is fit to the inner circumferential surface of the exterior case 111 and is rotatably accommodated in an accommodating unit which is substantially cylindrically shaped in the exterior case 111. A main body of a motor 115 is fixed to the inside of one end of the sensor holder 114, and a rotary shaft 115a projected from the motor 115 on a central axis O of the sensor holder 114 is pressed in a caved portion arranged on the central axis of the exterior case 111.

By driving the motor 115, the sensor holder 114 side fit in the exterior case 111 for accommodation is rotated relative to the exterior case 111.

The sensor holder 114 comprises a control circuit 116 near the motor 115, which rotates the motor 115 at a predetermined rotating speed. Near the control circuit 116, a battery 117 for supplying the power to the control circuit 116 and the motor 115 is arranged. In this case, the battery 117 is accommodated in a battery accommodating frame 118, and the battery accommodating frame 118 is pressed and is attached to the sensor holder 114.

As will be described later, the exterior case 111 is removed from the collected capsule medical device 103, and the sensor holder 114 is attached to the analyzing device 104 for analysis. In this case, the battery 117 is detached together with the battery accommodating frame 118 by pulling-out the battery accommodating frame 118 from the sensor holder 114.

On the outer circumferential surface containing a transparent member, a film-shaped sensor 120 is cylindrically arranged. The sensor 120 comprises a sensor surface 119 that is formed, with the width slightly larger than the size of the opening 112 in the longitudinal direction, by arranging a reagent layer for fixing the reagent that reacts to the examination target and converts it into a pigment so as to sense the cancer as the sensing target or bleeding, tumor marker, protein, carbohydrate, lipid, enzyme, drug, and immunity. Alternatively, the sensor 120 may comprise a film on which an antigen for connection to the examination target or protein such as the gene and lecithin is fixed on the sensor surface.

Specifically, referring to FIG. 16B, the sensor 120 is cylindrically shaped, and is structured by alternately forming a portion serving as the sensor surface 119 with a reagent layer in the circumferential direction and a portion without the reagent layer. That is, as enlargedly shown in FIG. 16C, the film-shaped sensor 120 comprises: a porous scattering layer 121a; a reagent layer 121b; and a transparent plastic layer 121c.

On the lower side of the transparent plastic layer 121c, a transparent layer comprising the sensor holder 114 is formed. As will be described later, the light is irradiated via the transparent layer containing the sensor holder 114, the reflected light is sensed, and the amount or concentration of the examination target is sensed.

A non-reagent layer 121d without the reagent layer 121b is arranged near the reagent layer 121b. The non-reagent layer 121d contains a member having the same optical property, except for the non-reaction to the reagent layer 121b and the examination target. As will be described later, when the analyzing device 104 performs the optical analysis, the analysis is executed by using the reagent layer 121b in consideration of the amount of reflected light using the no-reagent layer 121d (serving as reference data), thereby improving the sensing precision.

Referring to FIG. 16D, the motor 115 attached to the sensor holder 114 is intermittently rotated by a driving signal that is intermittently outputted (pulse driving signal shown by a cross line) under the control of the control circuit 116. Referring to FIG. 14, more specifically, for average five to eight hours from a time for swallowing the capsule medical device 103 by the patient 2 to a time for evacuating it out of the patient 2, the one rotation of the sensor surface 119 of the sensor 120 is set.

The capsule medical device 103 according to the fourth embodiment comprises a slit-shaped opening 112 with a narrow width at the exterior case 111, and the sensor 120 on the outer circumferential surface of the sensor holder 114 that is rotatably arranged in the exterior case 111. The motor 115 rotates the sensor holder 114 relative to the exterior case 111, thereby sequentially exposing (releasing) the sensor surface 119 serving as the detecting surface of the sensor 120 at the opening 112. Further, the exposed portion of the sensor surface 119 at the opening 112 performs the sensing operation. After a predetermined time, the sensor surface 119 used for sensing operation through the opening 112 is protected so that the sensor surface 119 is accommodated in the exterior case 111 at which the opening 112 is not formed.

After evacuating the capsule medical device 103 out of the body, the capsule medical device 103 is collected. Based on the reagent layer 121b on the sensor surface 119, the sensing target is sensed or is analyzed by the change in reflecting light which changes in reflecting property due to whether or not the reaction of the reagent layer 121b exists or the amount of reagent layer 121b.

Referring to FIG. 14, the analyzing device 104 has the base 123, and the base 123 has a caved portion on the top thereof.

The exterior case 111 of the collected capsule medical device 103, the battery accommodating frame 118, and the battery 117 are removed from the sensor holder 114. The rotary shaft 115a of the motor 115 on the sensor holder 114 is pressed in the caved portion.

To the base 123 a plurality of ring contacts 124a to 124c which always come into contact with a plurality of contacts conductive to the control circuit 116 arranged around the motor 115 are arranged.

The contacts 124a to 124c are connected to a setting and power supply unit 125 which is arranged on the base 123 via a wiring pattern arranged to the base 123. The setting and power supply unit 125 supplies power for operation to the control circuit 116 side, and performs the setting operation for setting the fast rotation of the control circuit 116. Thus, the motor 115 rotates faster than the case in the body cavity.

A projected piece 126 is arranged on the upper side of the base 123. A base end of a reflecting light measuring member 127 that is U-shaped is detachably fit into the caved portion arranged to the projected piece 126. The distal end side of the reflecting light measuring member 127 is arranged in the sensor holder 114. Further, a light-emitting element 128a and a light-receiving element 128b are attached to the distal end of the reflecting light measuring member 127. Light emitted from the light-emitting element 128a is irradiated to (the reagent layer 121b of) the sensor 120. The light-receiving element 128b senses the intensity of the light reflected by the surface or inside (of the reagent layer 121b) of the sensor 120.

The light-emitting element 128a and the light-receiving element 128b are connected to a measuring unit 129. The measuring unit 129 measures the amount of light emitted from the light-emitting element 128a, measures and analyzes the amount of sensing target on the reagent layer 121b from a signal which is received by the light-receiving element 128b and is photoelectrically converted, and stores and displays the analyzing result.

In the case of measuring the amount of reflecting light on the reagent layer 121b, the amount of reflecting light on the no-reagent layer 121d is referred to, thereby precisely sensing the sensing target as compared with the case of no no-reagent layer 121d.

Next, the operation according to the fourth embodiment will be described.

Referring to FIG. 14, in the case of examining the body, the patient 2 orally swallows the capsule medical device 103.

The swallowed capsule medical device 103 passes through the esophagus, the stomach, the small intestine, the large intestine, and the anus out of the body. Until evacuating the capsule medical device 103 out of the body, the capsule medical device 103 sequentially passes through the esophagus, the stomach, the small intestine, and the large intestine.

When an antigen exists as the sensing target on the sensor surface 119 that is externally exposed when the capsule medical device 103 sequentially passes through the esophagus and the stomach, the capsule medical device 103 uniquely reacts to the antigen.

In this case, the sensor holder 114 arranged in the exterior case 111 is intermittently and slowly rotated by the motor 115, thereby sequentially and externally exposing the sensor surface 119 of the sensor 120 at the opening 112. That is, the sensor surface 119 before reaction is protected in the inside of the exterior case 111 until it is used for the reaction.

The sensor surface 119 exposed at the opening 112 senses the component of the body fluid and the like. The sensor surface 119 after the sensing operation is protected by sequentially accommodating the sensor portions used for the sensing operation by the opening 112 in the exterior case 111 adjacent to the opening 112.

The sensing data on time series is fixed (held) to the reagent layer 121b by exposing (opening) the different sensor surfaces 119 at the opening 112. A medical stuff collects the extracorporeally-evacuated capsule medical device 103 and cleans it.

Then, the exterior case 111 is removed from the capsule medical device 103, and the battery accommodating frame 118 is pulled-out from the sensor holder 114.

Referring to FIG. 14, the motor 115 attached to the sensor holder 114 is rotated at the base 123 of the analyzing device 104. The rotation of the motor 115 rotates the motor main body, namely, the sensor holder 114 side in the case of the exterior case 111 into which the rotary shaft 115a is pressed (base 23 in this case) similarly to the case of the capsule medical device 103.

The reflecting light measuring member 127 optically senses or analyzes the sensing data corresponding to the presence or absence or the amount of the detecting target (reactive to the reagent) held to the reagent layer 121b, based on the measurement of the amount of reflecting beams irradiated to the reagent layer 121b. The optical sensing result (measuring result) is recorded to a measuring unit 129, and is displayed on a display unit (not shown).

According to the fourth embodiment, the sensing data on time series is obtained by sequentially exposing (opening) the different sensor surfaces 119 at the opening 112 arranged to the exterior case 111 of the capsule medical device 103. Therefore, the sensing target is continuously sensed in the body and the sensing result is precisely obtained with a simple structure.

The capsule medical device 103 has the holding structure in which the result reacted to the reagent layer 121b is held and therefore the capsule medical device 103 is realized with low costs.

When the sensing data held to the reagent layer 121b is optically obtained by the analyzing device 104, the motor 115 and the control circuit 116 as driving means forming a sensor surface exposing mechanism arranged on the capsule medical device 103 side are used, thereby simplifying the structure of the capsule medical system 101 with low costs.

Figure 17:
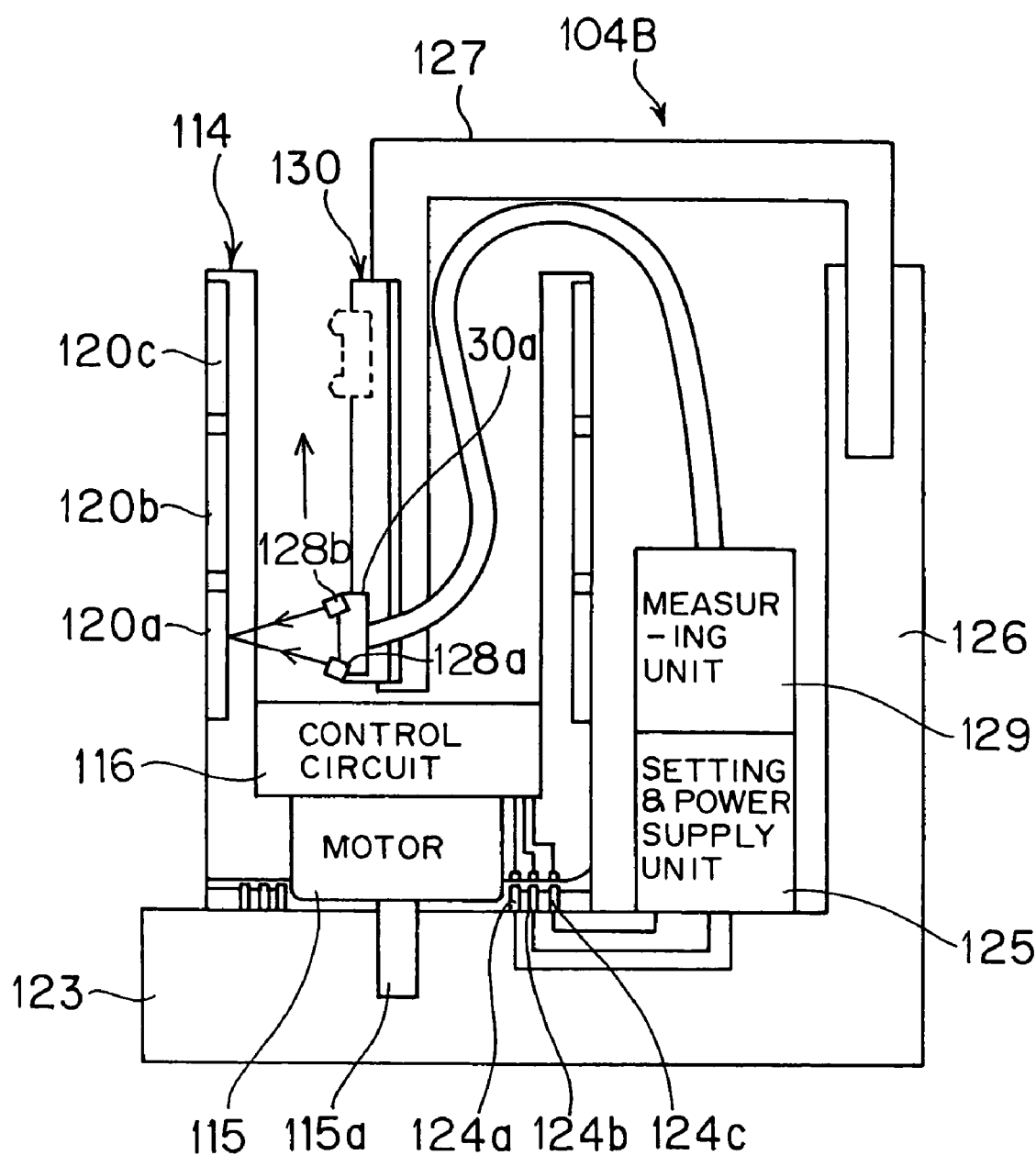
FIG. 17 is a diagram showing the structure of an analyzing device according to a modification.

FIG. 17 shows the structure in which a capsule medical device is collected and the sensor holder 114 is attached to a analyzing device 104B for analysis according to a modification.

Although the reagent layer 121b and the non-reagent layer 121d are arranged in the sensor 120 in the circumferential direction according to the fourth embodiment, the sensor 120 further has sensors 120a to 120c having reagent layers with different reagents in the axial direction of the sensor holder 114 (of the capsule medical device 103). That is, the sensors 120a, 120b, and 120c are arranged in such a way that the length of the slit opening 112 is divided into three. At the opening 112, three types of sensing targets are sensed. Other structures are the same as those according to the fourth embodiment.

When the capsule medical device is extracorporeally collected according to the modification, the exterior case 111 is removed similarly to the case according to the fourth embodiment. Further, the battery accommodating frame 118 is pulled-out from the sensor holder 114, the battery 117 is removed, and the sensor holder 114 is attached to the analyzing device 104B shown in FIG. 17.

The analyzing device 104B is structured by attaching, to the analyzing device 104 shown in FIG. 14, a linear motor 130 which moves the light-emitting element 128a and the light-receiving element 128b in the axial direction of the sensor holder 114 at the distal end of the reflecting light measuring member 27.

Further, the linear motor 130 comprises a movable unit 130a having a coil on the side of a stator containing a magnet, comprising the light-emitting element 128a and the light-receiving element 128b, thereby being moved in the axial direction of the sensor holder 114 along a guide rail (not shown).

The measuring unit 129 connected via a flexible cable 131 flows DC current to the coil of the movable unit 130a, thereby moving the movable unit 130a in the upper direction as shown by an arrow in FIG. 17. Or, the measuring unit 129 flows the DC current in the inverse direction to the coil of the movable unit 130a, thereby moving the movable unit 130a in the lower direction as shown by an arrow in FIG. 17. That is, the linear motor 130 moves the movable unit 130a having the light-emitting element 128a and the light-receiving element 128b to a position shown by a dotted line from a position shown by a solid line in FIG. 17 or to a position in the inverse direction.

That is, according to the modification, like the fourth embodiment, the sensor holder 114 is rotated and the light-emitting element 128a and the light-receiving element 128b are moved in the rotating axial direction, thereby sensing the plurality of different sensing targets by the different sensors 120a, 120b, and 120c.

In the description according to the fourth embodiment, the exterior case 111 side having the slit opening 112 is rotated and moved in the circumferential direction of the sensor holder 114 therein, thereby externally releasing (opening) the sensor surfaces 119.

Fifth Embodiment

Figure 18A:
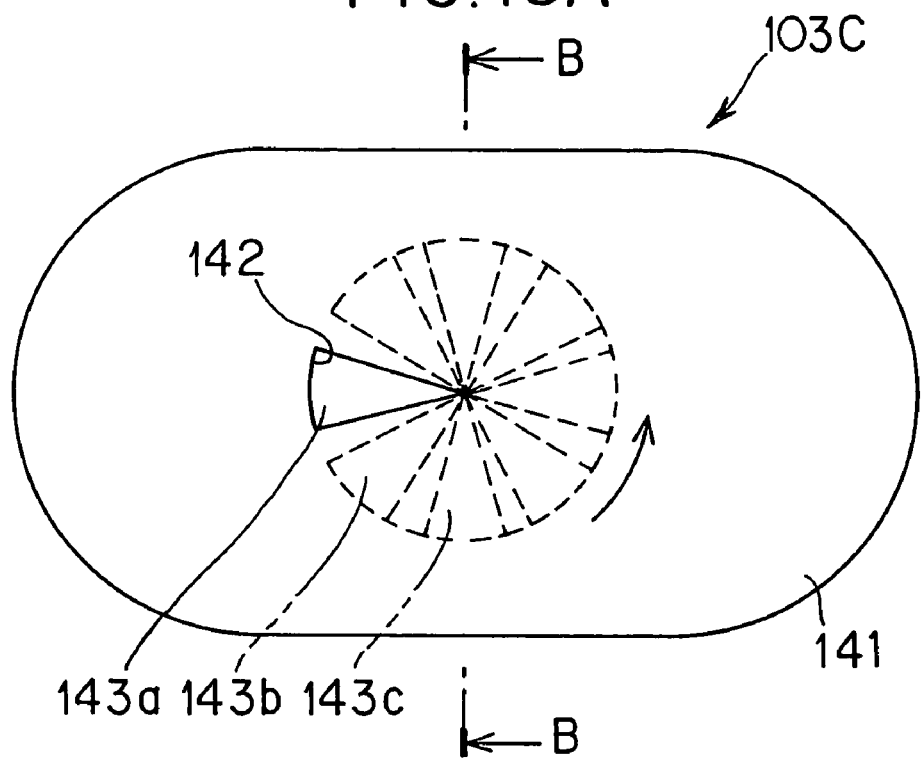
FIG. 18A is a plan view showing the structure of a capsule medical device according to a fifth embodiment of the present invention.
Figure 18B:
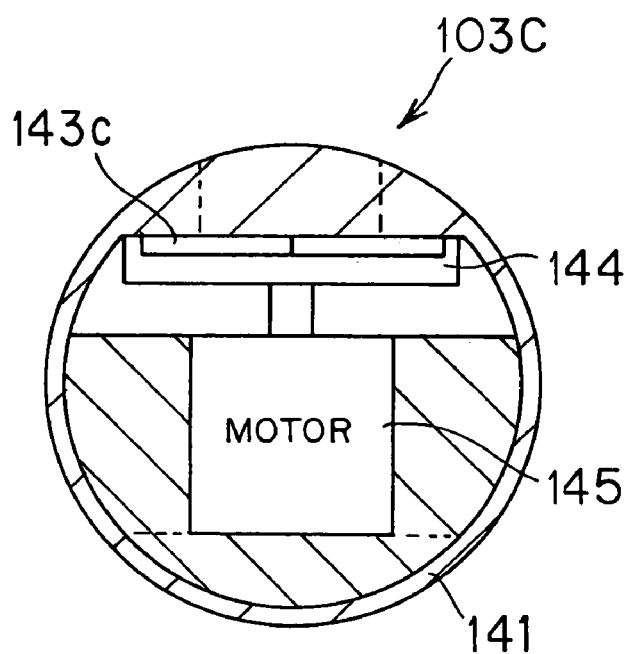
FIG. 18B is a cross-sectional view of a line connecting B in FIG. 18A.

Next, a description is given of a fifth embodiment of the present invention with reference to FIG. 18. FIG. 18A is a plan view showing a capsule medical device 103C according to the fifth embodiment. FIG. 18B is a diagram showing the internal structure by a line connecting B in FIG. 18A.

According to the fifth embodiment, the sensor surface exposing mechanism or sensor surface exposure control mechanism according to the fourth embodiment is modified.

That is, the capsule medical device 103C comprises: an exterior case 141; a fan-shaped opening 142 arranged to the exterior case 141; sensors 143a, 143b, and 143c arranged inside the opening 142; a disc-shaped sensor holder 144 having the sensors 143a, 143b, and 143c; and a motor 145 having a rotary shaft 145a. The sensor holder 144 is attached to the rotary shaft 145a of the motor 145. The rotation of the motor 145 is controlled by a control circuit (not shown in FIG. 18).

By rotating the motor 145, the fan-shaped sensors 143a, 143b, and 143c are sequentially exposed to the opening 142. The exposed sensors 143a, 143b, and 143c are sequentially covered with the exterior case 141 around the opening 142.

According to the fifth embodiment, at the opening 142 arranged to the exterior case 141 of the capsule medical device 103C similarly to the fourth embodiment, the sensor surfaces of the different sensors 143a, 143b, and 143c are sequentially exposed (opened), thereby obtaining measurement data on time series. Therefore, the sensing target is continuously sensed in the body and the sensing result is precisely obtained.

Sixth Embodiment

Figure 19A:
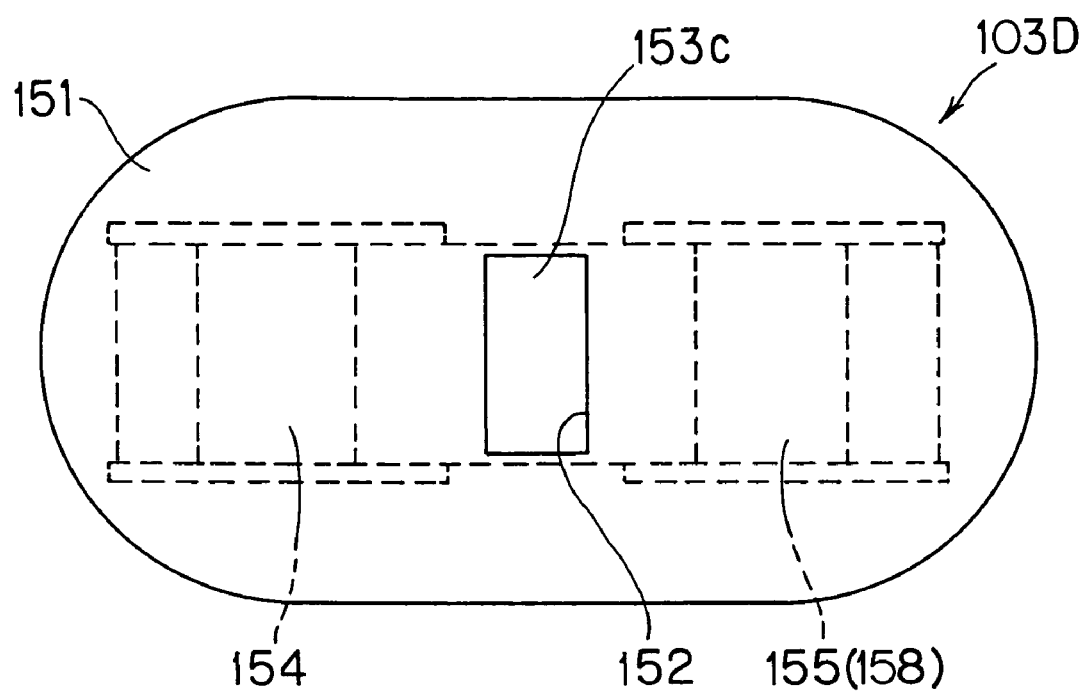
FIG. 19A is a plan view showing the structure of a capsule medical device according to a sixth embodiment of the present invention.
Figure 19B:
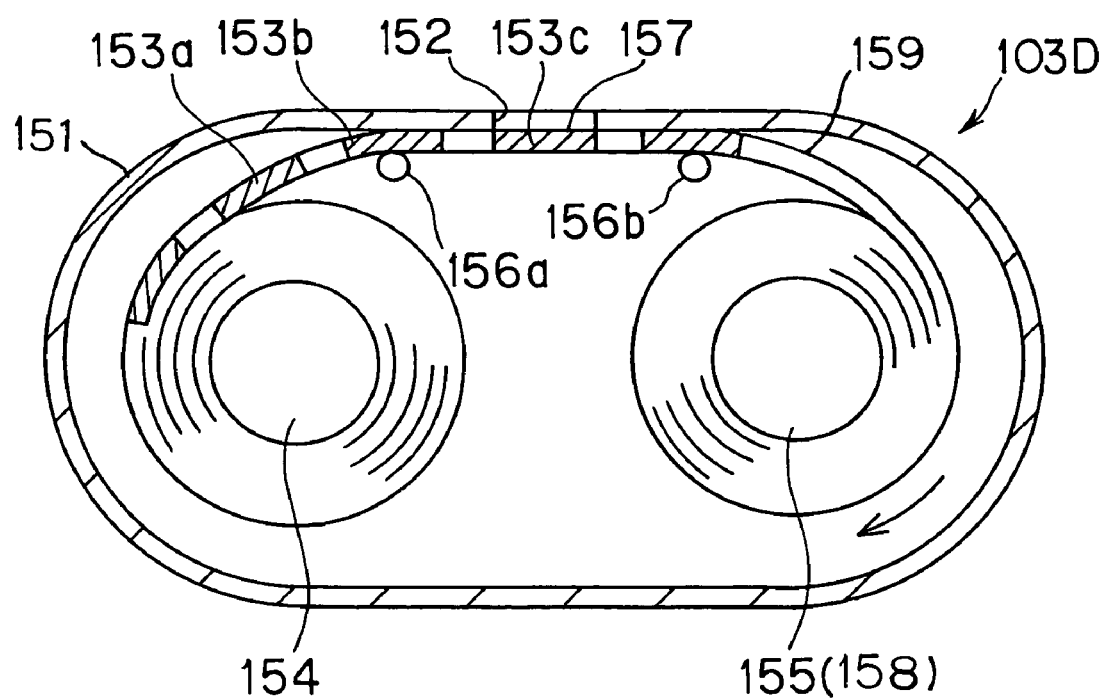
FIG. 19B is a longitudinal cross-sectional view showing the internal structure of the capsule medical device according to the sixth embodiment.

Next, the sixth embodiment of the present invention will be described with reference to FIG. 19. FIG. 19A is a plan view showing a capsule medical device 103D. FIG. 19B is a longitudinal cross-sectional view showing the internal structure.

According to the sixth embodiment, the sensor surface exposing mechanism or sensor surface exposure control mechanism according to the fourth embodiment is modified.

That is, the capsule medical device 103D comprises: a capsule-shaped exterior case 151; a substantially rectangular opening 152 near the center of the exterior case 151 in the longitudinal direction; sensors 153a, 153b, inside of the opening 152; a film 159 having the sensors 153a, 153b, . . . on the top surface thereof; a supply shaft 154; and a winding shaft 155. The film 159 is arranged between the supply shaft 154 and the winding shaft 155 to bridge them.

Referring to FIG. 19B, the supply shaft 154 and the winding shaft 155 are arranged near both ends of the exterior case 151 in the longitudinal direction. On the film 159, the sensors 153a, 153b, . . . are formed at a predetermined interval in the longitudinal direction of the film 159 so that the top surfaces of the sensors 153a, 153b, . . . become sensor surfaces 157. The structures of the film 159 and the sensors 153a, 153b, . . . may be the same as those according to the fourth embodiment, or the sensors 153a, 153b, . . . may be formed by arranging a reagent layer and a scattering layer on a white opaque film.

The film 159 is moved via rollers 156a and 156b and then reaches the opening 152. Further, the sensor surface 157 of the sensor 153i (i=a, b, . . . ) is exposed. After that, the sensor 153i exposed at the opening 152 is covered with an inner wall of the exterior case close to the opening 152, and is attached to the winding shaft 155 containing a rotating unit of a motor 158.

The rotation of the motor 158 is controlled by a control circuit (not shown). The motor 158 is rotated as shown by an arrow and thus the sensor 153i formed to the film 159 is wound to the winding shaft 155 on the outer circumferential surface of the motor 158. That is, the sensor 153i exposed at the opening 152 is sequentially moved to the winding shaft 155.

The exterior case 151 has a battery and a control circuit (not shown). A recording device (not shown) may record the amount of winding operation of the film 159 and the time for winding operation.

According to the sixth embodiment, the same advantages as those according to the fourth and fifth embodiments are obtained. The sensor 153i is formed on the film 159, thereby being wound. As compared with the fourth and fifth embodiments, the entire length of the sensor is set to be longer and the measurement data on time series is obtained with high resolution based on time unit.

The capsule medical device 103D is reduced in size. The structure of the capsule medical device 103D is simple. Thus, the costs are reduced.

Seventh Embodiment

Figure 20:
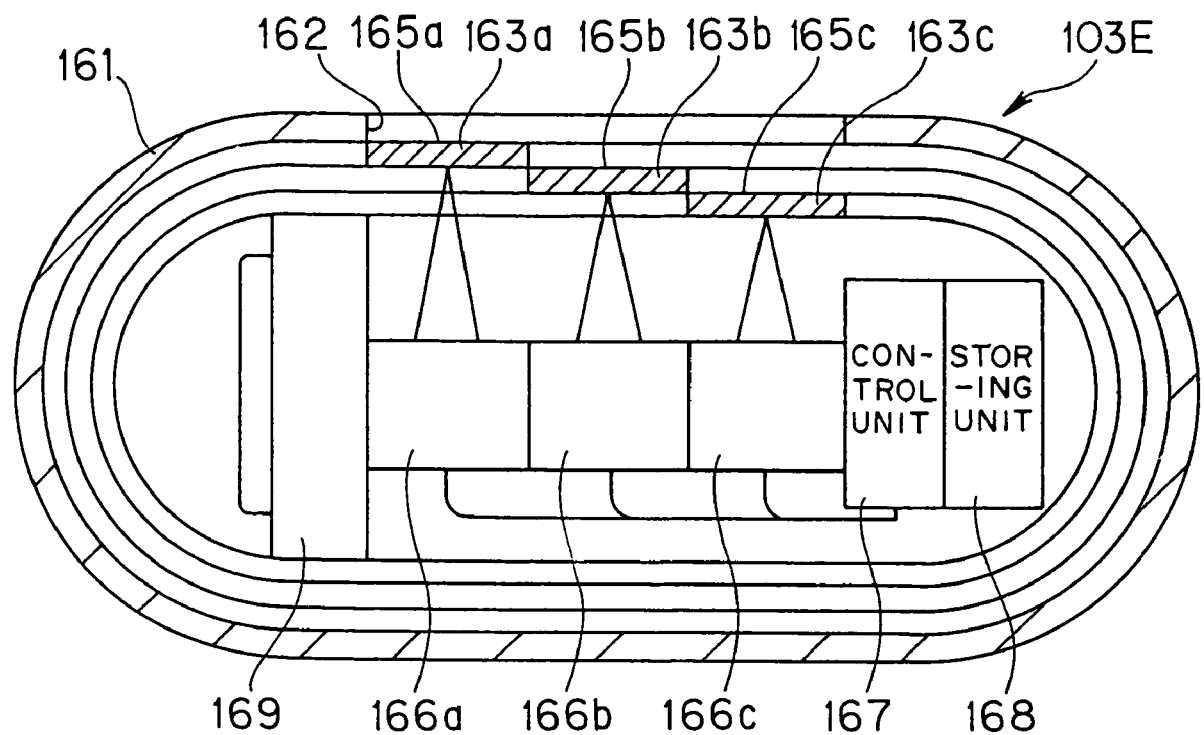
FIG. 20 is a longitudinal cross-sectional view showing the structure of a capsule medical device according to a seventh embodiment of the present invention.

Next, a seventh embodiment of the present invention will be described with reference to FIG. 20. FIG. 20 is a cross-sectional view showing the internal structure of a capsule medical device 103E according to the seventh embodiment.

The capsule medical device 103E comprises: a capsules-shaped exterior case 161; an opening 162 at the exterior case 161; and three laminated films of a first sensor 163a, a second sensor 163b, and a third sensor 163c on a first-layer film 164a, a second-layer film 164b, and a third-layer film 164c.

In this case, the first sensor 163a and the second sensor 163b are formed on the films 164a and 164b containing a substance digested in the gastrointestinal tract in the body.

A sensor surface 165a of the first sensor 163a is formed on the uppermost layer of the three-layer structure, and is first exposed at the opening 162 as compared with other sensors.

The sensor surface 165b of the second sensor 164b is positioned in the opening 162 to be formed on the film 164b at the adjacent position of the first sensor 164a. Normally, the sensor surface 165b is covered with the film 164a having the first sensor 163a. The film 164a is digested in the gastrointestinal tract and then the sensor surface 165b is exposed in the opening 162.

The sensor surface 165c of the third sensor 163c is positioned in the opening 162 to be formed on the film 164c at the adjacent position of the second sensor 163b. Normally, the sensor surface 165c is covered with the film 164b having the second sensor 163b and the film 164a thereon. The films 164a and 164b are digested in the gastrointestinal tract, and then the sensor surface 165c is exposed in the opening 162.

According to the seventh embodiment, the film 164c has measuring units 166a, 166b, and 166c having a light-emitting element and a light-receiving element. Light beams emitted from the light-emitting elements are focused to (the reagent layers of) the sensors 163a to 163c, and the reflected light is received by the light-receiving elements. The films 164b and 164c on the bottom layer (back) side of the sensor 163a are transparent, and the film 164c on the bottom (back) side of the sensor 163b is transparent.

The measuring units 166a to 166c are controlled by a control unit 167. The control unit 167 includes a timer (not shown), and controls the light emission from the light-emitting elements in the measuring units 166a to 166c, and stores, to a storing unit 168, sensing information indicating the change in signal level that is photoelectrically converted in accordance with the amount of light received by the light-receiving element. Further, the control unit 167 includes a battery 169, and the battery 169 supplies power to the control unit 167 and the like.

The control unit 167 first sets the measuring unit 166a to an operating state, thereby storing, to the storing unit 168, the information sensed by the sensor surface 165a of the sensor 163a. Thereafter, a predetermined time passes and then the control unit 167 sets the measuring unit 166b to an operating state and thus the control unit 167 monitors a value sensed by the measuring unit 166b. When the sensor 163b comes into contact with the body fluid and the level changes, the control unit 167 stops the operation of the measuring unit 166a. Further, the control unit 167 stores, to the storing unit 168, the sensing result of the measuring unit 166b.

The measuring unit 166b is set to an operating state, then, a predetermined time passes, and the control unit 167 sets the measuring unit 166c to an operating state. Further, the control unit 167 monitors a value sensed by the measuring unit 166c, then, when the sensor 163c comes into contact with the body fluid and the level changes, the control unit 167 stops the operation of the measuring unit 166b. Further, the control unit 167 stores, to the storing unit 168, the sensing result of the measuring unit 166c.

In this case according to the seventh embodiment, the measurement data on time series is obtained in the body cavity, and the measurement data is stored in the storing unit 168. Therefore, when the sensing results of the sensors 163a to 163c easily change through the time passage, the measurement data without the influence therefrom is obtained.

The marking structure according to the third embodiment may be combined to the structure described according to the seventh embodiment. The marking operation may be performed in association with the sensing operation of the sensors, and the marking information may be stored in the storing unit in association with sensor sensing information. Thus, the same advantage as the advantage for certainly specifying the sensed position according to the third embodiment is obtained.

Eighth Embodiment

Figure 21:
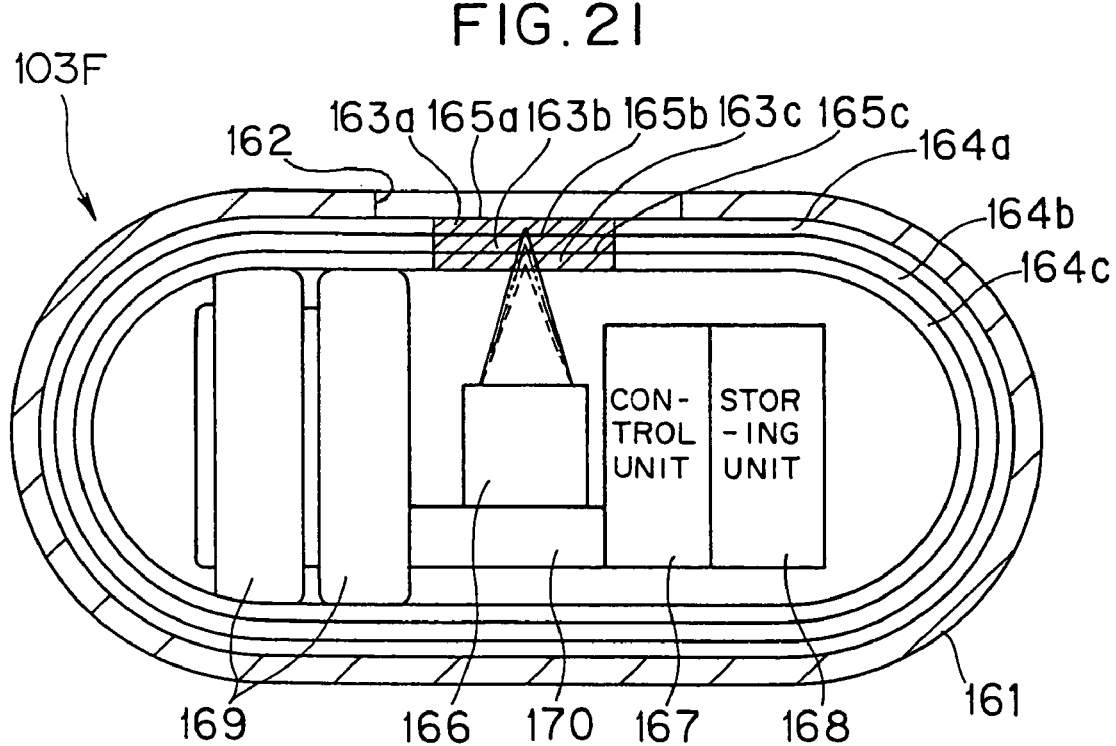
FIG. 21 is a cross-sectional view showing the structure of a capsule medical device according to an eighth embodiment of the present invention.

Next, an eighth embodiment of the present invention will be described with reference to FIG. 21 according to the eighth embodiment. FIG. 21 is a cross-sectional view showing the internal structure of a capsule medical device 103F according to the eighth embodiment.

The capsule medical device 103F has the structure that is obtained by modifying the capsule medical device 103E shown in FIG. 20. Specifically, the sensors 163a to 163c are deviated and are laminated so as to prevent the overlapping in the capsule medical device 103E shown in FIG. 20. However, according to the eighth embodiment, the sensors 163a to 163c are laminated to be overlapped. The films 164a to 164c around the sensors 163a to 163c are set, facing the opening 162.

Further, the capsule medical device 103E shown in FIG. 20 has the three measuring units 166a to 166c for measuring the sensing results of the sensors 163a to 163c. However, according to the eighth embodiment, the capsule medical device 103F has only one measuring unit 166, and the focusing distance (focusing position) is sequentially changed from the sensor 163a to the sensor 163b and the sensor 163c, as will be described later. The measuring result of the measuring unit 166 for the sensor 163i at the focusing position is stored in the storing unit 168.

The measuring unit 166 is attached to a piezoelectric unit 170 serving as changing means of the focusing distance of the light beams, and the piezoelectric unit 170 is controlled by the control unit 167.

The control unit 167 applies a DC voltage to the piezoelectric unit 170, and changes the thickness in the thickness direction of the piezoelectric unit 170 in the thickness direction to which the measuring unit 166 is attached. Then, the light beams from the light-emitting device is focused on the sensor surface 163i, and the control unit 167 controls the operation for properly receiving the reflected light by the light-receiving element.

That is, the control unit 167 controls the piezoelectric unit 70 so that the position of the sensor 163a enters the focusing state. A predetermined time passes, and the control unit 167 controls the operation for setting the position of the sensor 163b at the focusing position about the time when the first film 164a having the sensor 163a is digested and is absent. Further, a predetermined time passes, and the control unit 167 controls the operation for setting the position of the sensor 163c at the focusing position about the time when the second film 164b having the sensor 163b is digested and is absent.

Under the above control operation, the same advantage as that according to the seventh embodiment is realized when the capsule medical device 103F has the one measuring unit 166.

Ninth Embodiment

Figure 22:
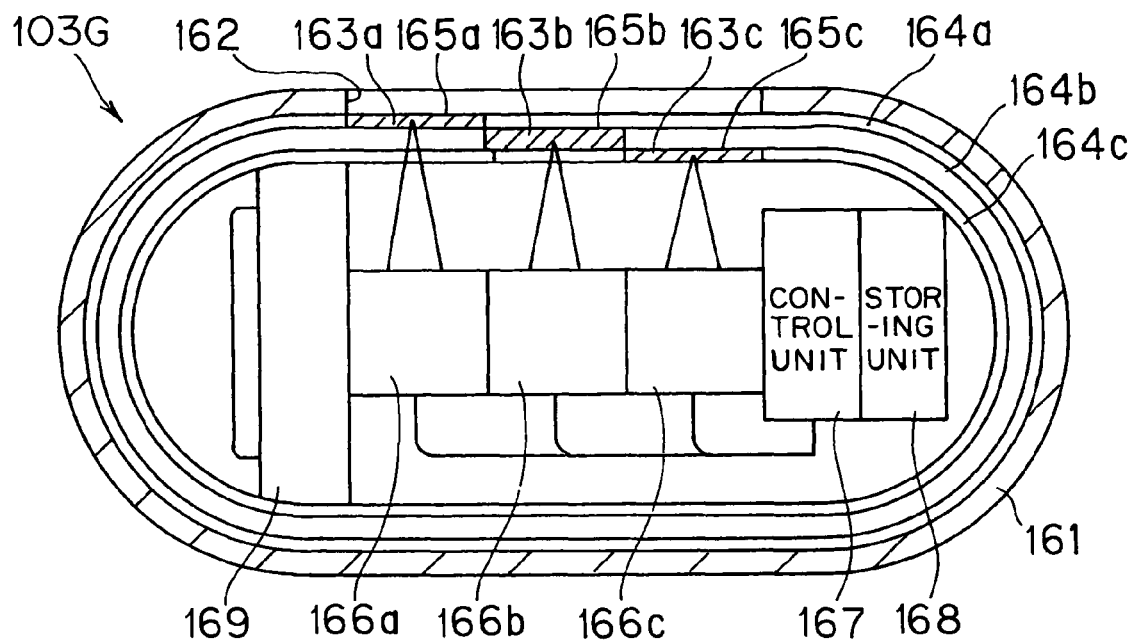
FIG. 22 is a cross-sectional view showing the structure of a capsule medical device according to a ninth embodiment of the present invention.

Next, a ninth embodiment of the present invention will be described with reference to FIG. 22 according to the ninth embodiment. FIG. 22 is a cross-sectional view showing the internal structure of a capsule medical device 103G according to the ninth embodiment.

The capsule medical device 103G has the structure that is obtained by modifying the capsule medical device 103E shown in FIG. 20. Specifically, the capsule medical device 103E shown in FIG. 20 is modified so that the thicknesses of the films 164a to 164c having the sensors 163a to 163c are changed to examine the sensing target positions.

Specifically, the thickness of the layer is changed in accordance with the passing time of the organ such as the stomach, small intestine, or large intestine and the digestive operation in the organ by the digestive fluid. Or, the layer corresponding to the position to be examined more precisely may be thicker than another layer. Further, the thickness may be set so that the proper or certain examination is possible at the position of which information to be obtained.

Referring to FIG. 22, the film 164a is formed to be thin, the film 164b is formed to be thick, and the film 164c is formed to be thin.

As a consequence, the sensing target position is properly examined. Further, the proper or certain examination is possible at the position of which information to be obtained.

Other structures have the same advantages as those of the capsule medical device 103E shown in FIG. 20. The ninth embodiment can be applied to the embodiment shown in FIG. 21.

Tenth Embodiment

Figure 23:
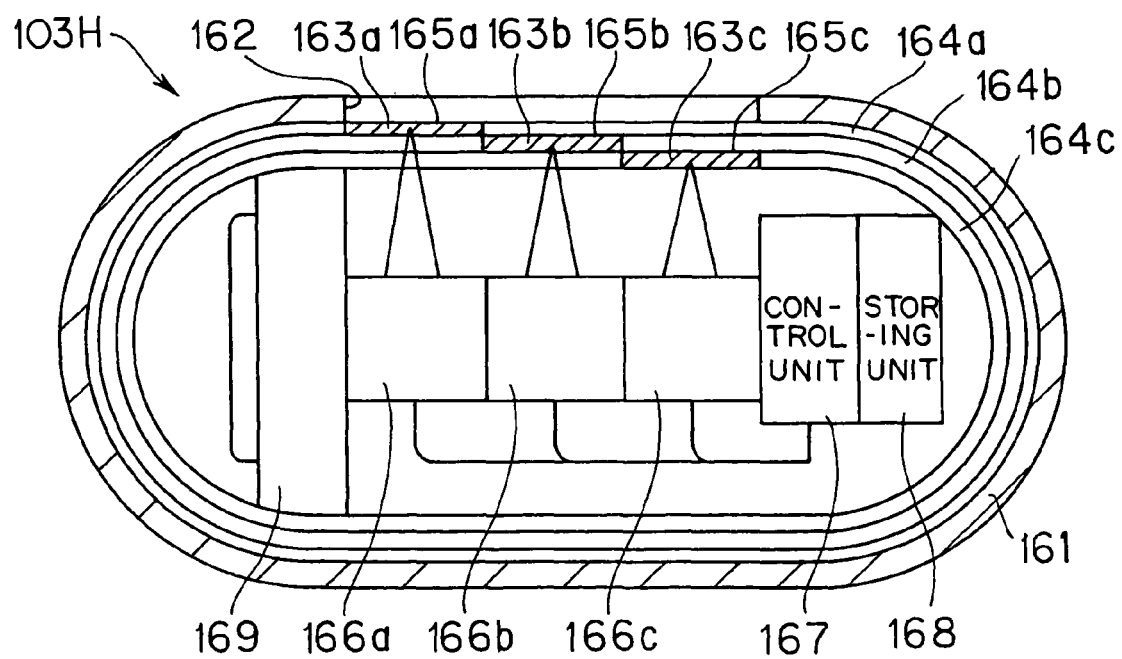
FIG. 23 is a longitudinal cross-sectional view showing the structure of a capsule medical device according to a tenth embodiment of the present invention.

Next, a tenth embodiment of the present invention will be described with reference to FIG. 23. FIG. 23 is a cross-sectional view showing the internal structure of a capsule medical device 103H according to the tenth embodiment.

The capsule medical device 103H has the structure that is obtained by modifying the capsule medical device 103E shown in FIG. 20. Specifically, in the capsule medical device 103E shown in FIG. 20, the film 164a contains a substance that is easily digested in the stomach, and the film 164b contains a substance that is digested in the small intestine. The film 164c may contain a substance that is easily digested in the large intestine.

According to the tenth embodiment, the stomach, small intestine, and large intestine are sequentially examined on time series and the examined data is stored.

Eleventh Embodiment

Figure 24A:
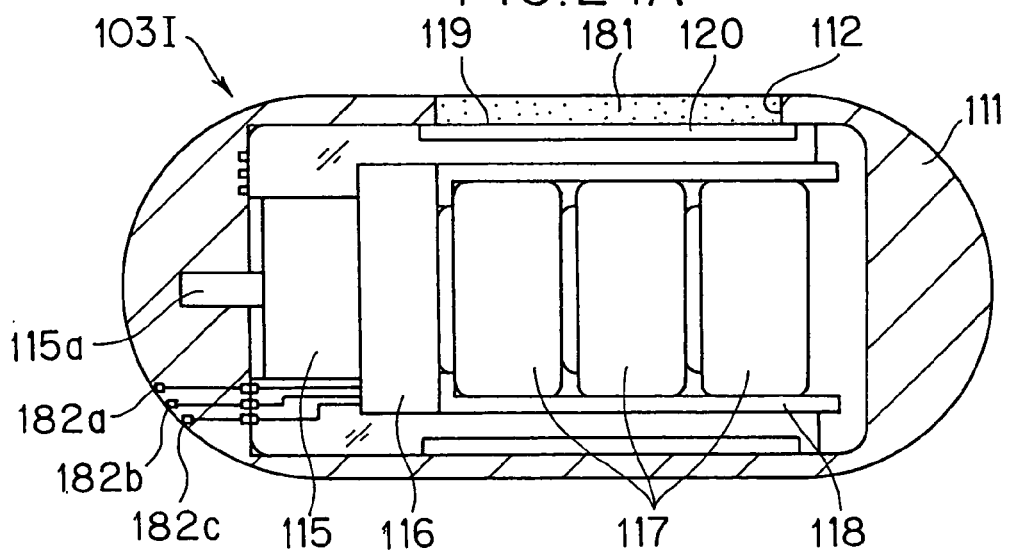
FIG. 24A is a diagram showing the structure of a capsule medical device according to an eleventh embodiment of the present invention.
Figure 24B:
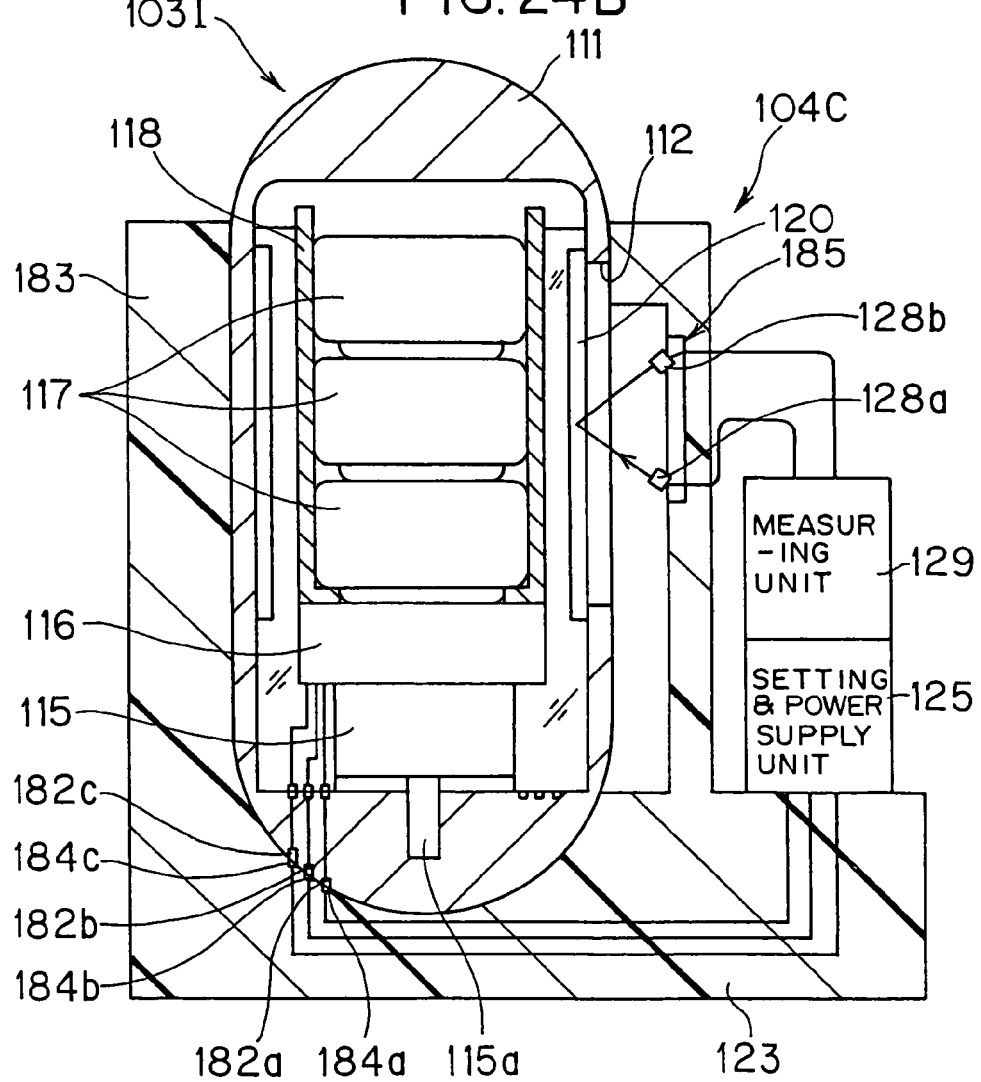
FIG. 24B is a diagram showing the structure of an analyzing device which analyzes data by attaching the capsule medical device according to the eleventh embodiment of the present invention.

Next, an eleventh embodiment of the present invention will be described with reference to FIG. 24. FIG. 24A shows a capsule medical device 103I according to the eleventh embodiment. FIG. 24B shows an analyzing device 104C which performs the collection and the examination. According to the eleventh embodiment, a capsule medical device having a sensor extracorporeally collects the sensing data and then analyzes the sensing data held in the sensor without change by using the analyzing device.

Referring to FIG. 24A, the capsule medical device 103I is formed by attaching a filtering member 181 to the opening 112 in the capsule medical device 103 shown in FIG. 16A.

The contacts arranged to the sensor holder 114 connected to the control circuit 116 are connected to contacts 182a to 182c arranged near the outer surface via ring-shaped contacts of the exterior case 111 in the capsule medical device 103I. In the usual examining time, the contacts 182a to 182c are covered with an insulating member.

According to the eleventh embodiment, the filtering member 181 is arranged, thus, the uppermost layer of the sensor 120 having the sensor surface 119 does not have the scattering layer 121a, but the reagent layer 121b faces the uppermost layer of the sensor 120. Other structures are the same as those of the capsule medical device 103 shown in FIG. 16A.

The examination in the body of the capsule medical device 103I is the same as that according to the fourth embodiment. The advantages according to the eleventh embodiment are the same as those according to the fourth embodiment.

Meanwhile, in the case of collecting the capsule medical device 103I which is extracorporeally evacuated and measuring (analyzing) the amount of pigment which is reactive to the sensing target fixed (held) to the sensor 120, the capsule medical device 103I is cleaned, the filtering member 181 attached to the opening 112 is removed, and an analyzing device 104C shown in FIG. 24B is used.

The base 123 in the analyzing device 104 shown in FIG. 14 has an accommodating member 183 for fitting and accommodating the capsule medical device 103I in the analyzing device 104C. The accommodating member 183 accommodates the capsule medical device 103I, and the contacts on the side of the capsule medical device 103I come into contact with the contacts 184a to 184c arranged to the accommodating member 183.

The contacts 184a to 184c are connected to the setting and power supply unit 25 similarly to the analyzing device 104 shown in FIG. 14, thereby rotating the motor 115 in the capsule medical device 103I.

The accommodating member 183 has a reflecting light measuring unit 185 corresponding to the reflecting light measuring member 127 in the analyzing device 104 shown in FIG. 14. The reflecting light measuring unit 185 has a light-emitting element 128a and a light-receiving element 128b for measuring the light. Thus, the light emitted by the light-emitting element 128a is irradiated to (the reagent layer 21b of) the sensor 120 and the light-receiving element 128b senses the intensity of the light reflected by (the reagent layer 121b of) the sensor 120. The light-emitting element 128a and the light-receiving element 128b connected to the measuring unit 129.

Other structures are the same as those of the analyzing device 104 shown in FIG. 14. In the analyzing device 104C according to the eleventh embodiment, the filtering member 181 attached to the opening 112 is removed without resolving the capsule medical device 103I, thereby sensing the sensing information held by the sensor 120.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule medical device having a chemical sensor used for sensing operation, comprising:
   a capsule casing;
   a chemical sensor arranged in the capsule casing;
   a heater arranged on a back side of the chemical sensor in the capsule casing; and
   a recovery device, arranged in the capsule casing, configured to recover the chemical sensor substantially to an initial state thereof so as to use the chemical sensor for sensing operation a plurality of times or continuously by controlling heating of the chemical sensor by the heater so as to dry a sensor surface used for sensing operation of the chemical sensor and to remove an undesired substance on the sensor surface.

2. A capsule medical device according to claim 1, further comprising: an opening/closing cover which protects the sensor surface of the chemical sensor.

3. A capsule medical device according to claim 2, further comprising: a control unit controlling the two adjacent chemical sensors, wherein one of the chemical sensors is covered with the cover, the other chemical sensor that is not covered with the cover performing the sensing operation.

4. A capsule medical device according to claim 1, wherein the sensor surface recovery device comprises a cleaning unit which cleans the sensor surface of the chemical sensor by a cleaning solution.

5. A capsule medical device according to claim 1, further comprising: a control unit which periodically operates the sensor surface recovery device.

6. A capsule medical device according to claim 1, further comprising:
   an illuminating unit which illuminates the inside of the living body;
   an image pick-up unit which picks-up an image of an illuminated portion; and
   an image pick-up control unit which controls the illuminating unit, the image pick-up unit, and the chemical sensor in association therewith.

7. A sensing method of a capsule medical device having a chemical sensor, comprising:
   a first step of introducing the capsule medical device in the body;
   a second step of sensing an examination target by the chemical sensor; and
   a third step of, after the second step, performing recovery processing for resetting the chemical sensor substantially to an initial state thereof by heating the chemical sensor so as to dry a sensor surface used for sensing operation of the chemical sensor and to remove an undesired substance on the sensor surface at a set timing.

8. A sensing method of a capsule medical device according to claim 7, wherein the inside of the body is photographed in association with the sensing operation in the second step.

* * * * *